US010436028B2

United States Patent
Dai et al.

(10) Patent No.: US 10,436,028 B2
(45) Date of Patent: Oct. 8, 2019

(54) METHODS AND SYSTEMS FOR OBTAINING HIGH-RESOLUTION SPECTRAL DATA OF FORMATION FLUIDS FROM OPTICAL COMPUTING DEVICE MEASUREMENTS

(71) Applicant: HALLIBURTON ENERGY SERVICES, INC., Houston, TX (US)

(72) Inventors: Bin Dai, Spring, TX (US); Christopher Michael Jones, Houston, TX (US); Dingding Chen, Tomball, TX (US); Jing Shen, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 159 days.

(21) Appl. No.: 15/535,693

(22) PCT Filed: Sep. 22, 2016

(86) PCT No.: PCT/US2016/053048
§ 371 (c)(1),
(2) Date: Jun. 13, 2017

(87) PCT Pub. No.: WO2018/056976
PCT Pub. Date: Mar. 29, 2018

(65) Prior Publication Data
US 2019/0063215 A1 Feb. 28, 2019

(51) Int. Cl.
*G01N 21/00* (2006.01)
*E21B 49/08* (2006.01)
(Continued)

(52) U.S. Cl.
CPC ............ *E21B 49/08* (2013.01); *E21B 44/00* (2013.01); *E21B 47/00* (2013.01); *E21B 47/12* (2013.01);
(Continued)

(58) Field of Classification Search
CPC ............ G01N 21/8507; G01N 21/31; G01N 21/0303; G01N 21/59; G01N 21/05
(Continued)

(56) References Cited

U.S. PATENT DOCUMENTS

| 6,529,276 B1 | 3/2003 | Myrick |
| 2004/0069942 A1 | 4/2004 | Fujisawa et al. |

(Continued)

FOREIGN PATENT DOCUMENTS

| CN | 103247034 A | 1/2016 |
| WO | WO-2009/091763 A2 | 7/2009 |

(Continued)

OTHER PUBLICATIONS

Piche, "Nonnegative color spectrum analysis filters from PCT characteristic spectra," J Opt Soc Am A, 2002, 14 pages.
(Continued)

*Primary Examiner* — Md M Rahman
(74) *Attorney, Agent, or Firm* — Gilliam IP PLLC

(57) ABSTRACT

A system includes an optical computing device having an optical multiplexer that receives a sample light generated by an optical interaction between a sample and an illumination light is provided. The system includes sensing elements that optically interact with the sample light to generate modified lights, and a detector that measures a property of the modified lights separately. Linear and nonlinear models for processing data collected with the above system to form high-resolution spectra are also provided. Methods for designing optimal optical multiplexers for optimal reconstruction of high-resolution spectra are also provided.

10 Claims, 21 Drawing Sheets

(51) Int. Cl.
    *G01N 21/31* (2006.01)
    *E21B 44/00* (2006.01)
    *E21B 47/00* (2012.01)
    *E21B 47/12* (2012.01)
    *G01N 21/33* (2006.01)
    *G01N 21/3577* (2014.01)
    *G01N 21/359* (2014.01)
    *E21B 47/10* (2012.01)

(52) U.S. Cl.
    CPC ........... *G01N 21/31* (2013.01); *G01N 21/314* (2013.01); *G01N 21/33* (2013.01); *G01N 21/359* (2013.01); *G01N 21/3577* (2013.01); *E21B 47/102* (2013.01); *G01N 2021/3155* (2013.01); *G01N 2021/3174* (2013.01); *G01N 2201/1293* (2013.01); *G01N 2201/1296* (2013.01)

(58) Field of Classification Search
    USPC ........................................................... 356/436
    See application file for complete search history.

(56) References Cited

U.S. PATENT DOCUMENTS

| | | |
|---|---|---|
| 2006/0142955 A1 | 6/2006 | Jones et al. |
| 2009/0078860 A1 | 3/2009 | Kischkat et al. |
| 2010/0195105 A1 | 8/2010 | Myrick et al. |
| 2010/0253935 A1* | 10/2010 | MacKinnon ............... G01J 1/32 356/51 |
| 2011/0108720 A1* | 5/2011 | Ford ........................ E21B 49/08 250/262 |
| 2013/0284897 A1 | 10/2013 | Freese et al. |
| 2013/0284900 A1* | 10/2013 | Freese ..................... G01N 21/17 250/208.2 |
| 2013/0287061 A1 | 10/2013 | Freese et al. |
| 2014/0022544 A1 | 1/2014 | Kurokawa et al. |
| 2014/0352953 A1 | 12/2014 | Gao et al. |
| 2014/0360257 A1 | 12/2014 | Indo et al. |
| 2015/0212232 A1 | 7/2015 | Perkins et al. |
| 2016/0048627 A1 | 2/2016 | Perkins et al. |
| 2016/0054285 A1 | 2/2016 | Freese et al. |
| 2016/0076367 A1 | 3/2016 | Freese et al. |
| 2016/0130696 A1 | 5/2016 | Price et al. |
| 2016/0146667 A1 | 5/2016 | August et al. |
| 2016/0169794 A1 | 6/2016 | Powers et al. |

FOREIGN PATENT DOCUMENTS

| | | |
|---|---|---|
| WO | WO-2015112177 A1 | 7/2015 |
| WO | 2015126386 A1 | 8/2015 |
| WO | 2016108809 A1 | 7/2016 |

OTHER PUBLICATIONS

International Search Report and Written Opinion from PCT/US2016/05348, dated Jun. 1, 2017.
EP Application Serial No. 16916946.3, Partial European Search Report, dated Mar. 14, 2019, 15 pages.
EP Application Serial No. GB16916946.3, Comm. Pursuant to Rules 70(2) and 70a(2) EPC, dated Jul. 16, 2019, 1 page.
EP Application Serial No. GB 16 916 946.3; Extended European Search Report; dated Jun. 28, 2019, 25 pages.
"Compression Line Spectrum Estimation with Clustering and Interpolation", 2016 Annual Conference on Information Science and Systems (CISS), IEEE, Mar. 16, 2016 (Mar. 16, 2016), pp. 572-577, XP032895912.

* cited by examiner

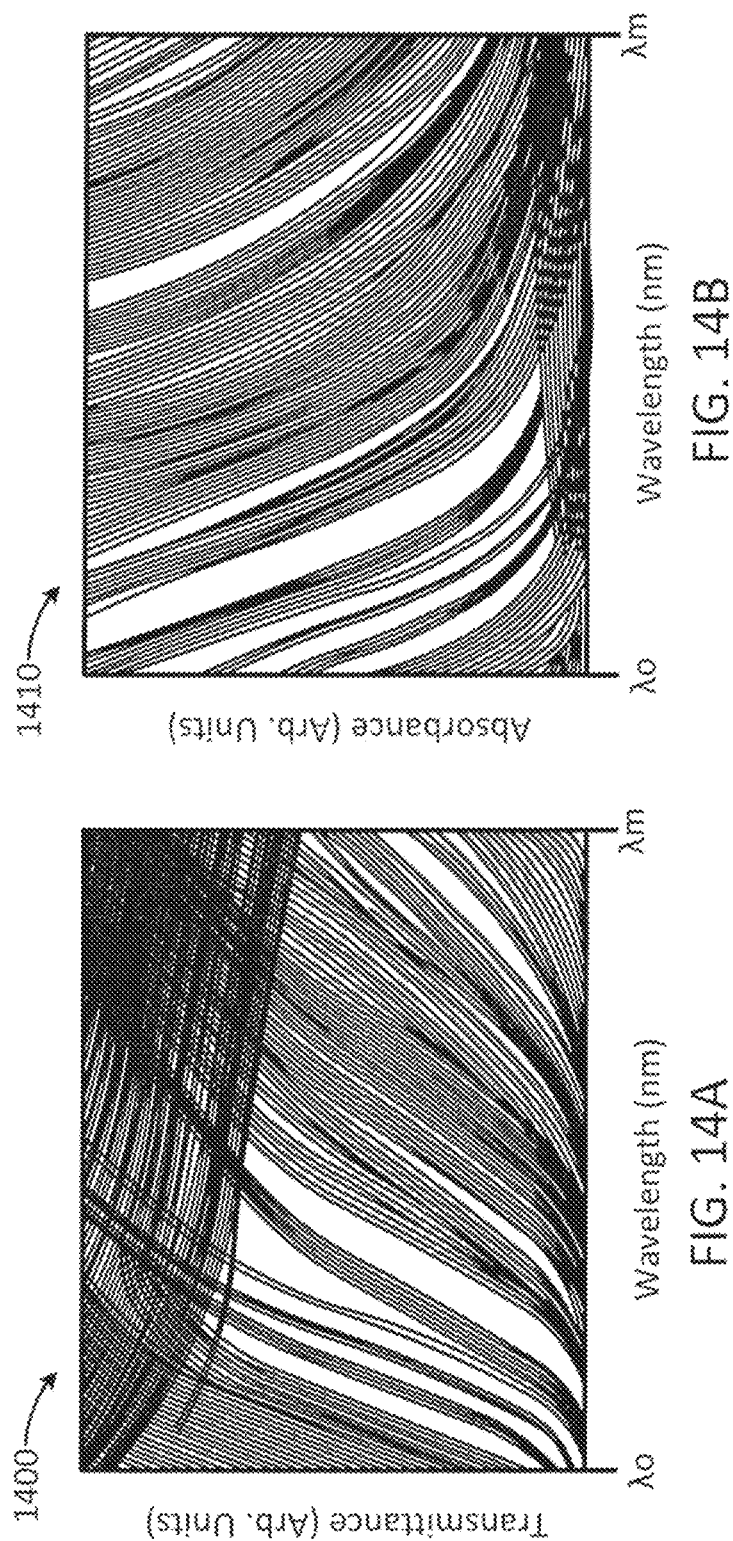

METHODS AND SYSTEMS FOR OBTAINING HIGH-RESOLUTION SPECTRAL DATA OF FORMATION FLUIDS FROM OPTICAL COMPUTING DEVICE MEASUREMENTS

BACKGROUND

In the field of oil and gas exploration and production, sample characterization of reservoir or wellbore fluid compositions is desirable to determine the quality of a product or the condition of a container, a wellbore, or a pipeline, or to adjust and modify a drilling parameter. The gold standard of spectroscopic measurement in terms of bandwidth and resolution is Fourier-Transform-Infrared (FTIR) spectrometry. Unfortunately, FTIR instruments with high resolving power are complex, delicate instruments not suitable for field operations. Some high-resolution spectrometers use highly-resolving angle/location dispersive devices such as narrow band filters, echelons, or diffraction gratings. However, these types of spectrometers typically have low optical throughput, thus requiring high detector sensitivity and long collection time. Some devices sacrifice measurement resolution to compactness and robustness of sensors used in the field. However, these approaches preclude the use of data collected with less-than ideal sensors in a post-production data analysis, leading to the loss of valuable information.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

FIG. 14A illustrates transmittance spectra reconstructed from the raw transmittance spectra in FIG. 13B using a MISO model.

FIG. 14B illustrates absorbance spectra corresponding to the transmittance spectra of FIG. 14A.

In the figures, elements or steps having the same or similar reference numerals have the same or similar description and configuration, unless stated otherwise.

DETAILED DESCRIPTION

Figure 1A:
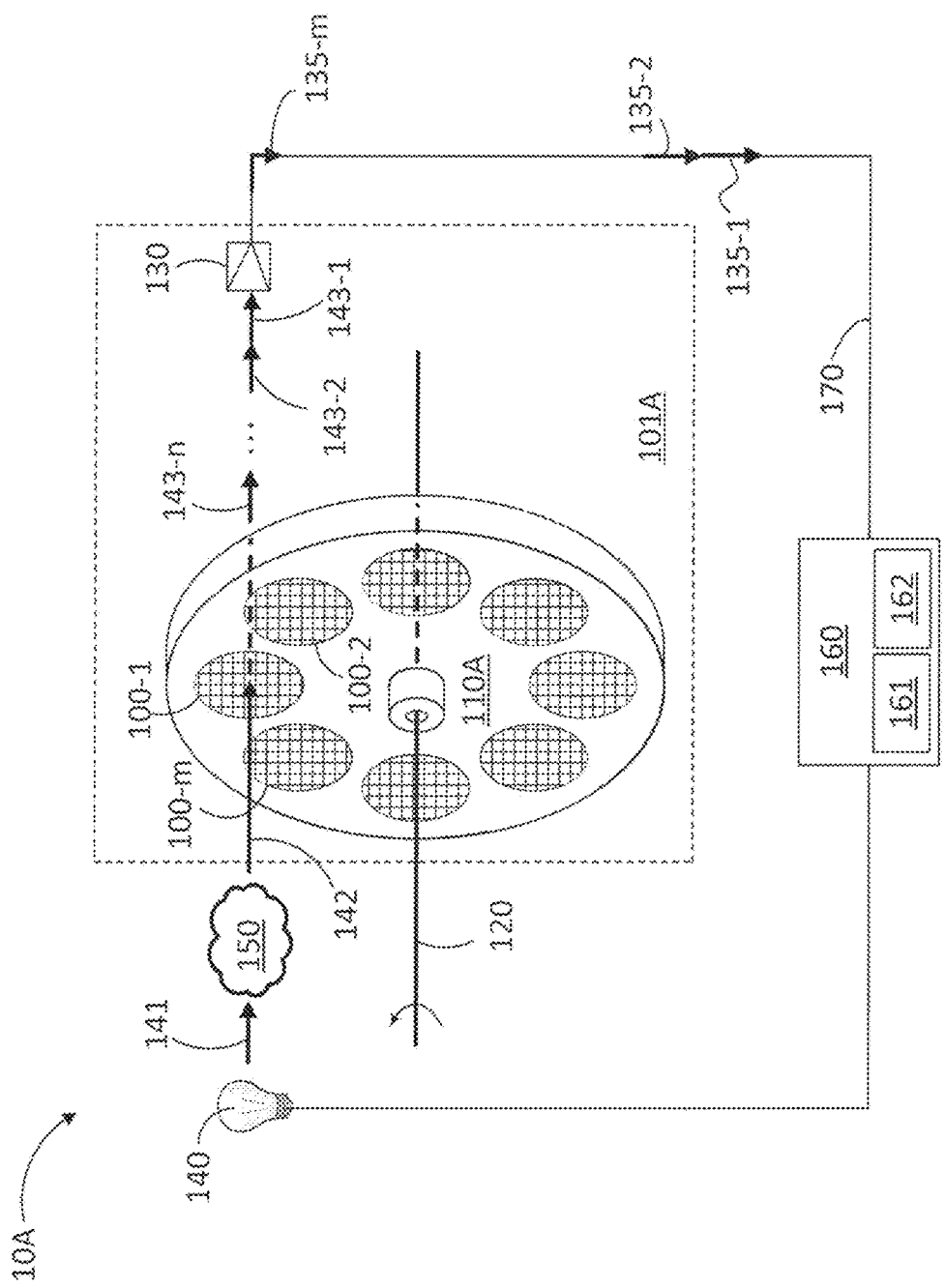
FIGS. 1A and 1B illustrate systems for obtaining high-resolution spectral data of a formation fluid from an optical computing device.

The present disclosure relates to systems, devices and methods for obtaining high-resolution spectral data of formation fluids from optical computing device measurements in the oil and gas exploration and extraction industry. In some embodiments, the high-resolution spectral data is obtained in real-time and in the field. Yet in other embodiments, the high-resolution spectral data is processed remotely, at a different time, after the sensor data is collected and stored in real-time in the field.

Spectroscopy-based optical fluid analysis is desirable in current practice for identifying downhole fluid characteristics. The full-range spectroscopy data of selected fluid samples can be measured at a standard Optical-Pressure, Volume and Temperature (PVT) laboratory, and used with various sensing elements (e.g., optical filters) having different wavelength bands to extract features which can be linearly or nonlinearly correlated to the known fluid compositions and properties. These sensing elements can be built into an optical computing device as multi-band elements, and installed on downhole optical tools for real-time data processing in predicting compositions and properties of new formation fluids. For advanced applications, however, it is desirable to convert integrated sensor responses on formation fluid during the operation of sampling back to a high-resolution spectrum. The recovered high-resolution spectrum enables a better synchronization between new data with data in an existing database, filling gaps in a current fluid spectroscopy library, and facilitating potential re-modeling applications with inclusion of an estimated new fluid spectrum.

In some embodiments disclosed herein, a compressive sensing principle is applied to design optical computing devices, resulting in a simplified and rugged spectrometer that can be used in harsh environments, such as downhole conditions, and still provide high-resolution spectra. Accordingly, this disclosure allows high-resolution, high quality optical spectra to be measured and reconstructed with a simplified optical instrument using a compressive sensing principle. In the compressive sensing principle, a sparse dictionary-based spectral representation improves spectral reconstruction as compared to other techniques, such as factor space-based spectral representation. The improved spectral quality of compressive sensing enhances measurement accuracy and precision.

This disclosure includes optical computing devices with multiple competitive advantages: a simplified compressive sensing instrument reduces the cost of manufacture and maintenance service, improves reliability in field operation and improves measurement quality. Recording high quality and high-resolution spectra of downhole fluids in visible (VIS) and short near-infrared (NIR) spectral regions allows accurate determination of complex compositions and physical properties such as, but not limited to: gas-oil-ratio (GOR), methane concentration, ethane concentration, propane concentration, asphaltenes, color, API, density, saturates, aromatics, resins, $CO_2$, $H_2S$, synthetic drilling filtrate and wax. In some embodiments, high quality spectral data enables a more accurate determination of drilling mud filtrate contamination level, allowing high quality, low contamination formation fluids to be sampled. High-resolution spectral data recovered as disclosed herein also allows reservoir connectivity information to be derived. For example, in multiple samples collected at different depths along a borehole, similar sample spectra with nearly identical transmittance at the wavelength range of interest may indicate that obtained samples are from a connected subterranean pools; otherwise, there is a high likelihood that the two fluids come from disconnected reservoirs.

Some embodiments contemplated herein provide robust nonlinear inversion methods in estimating fluid color spectrum using cross-wavelength-band information available in downhole optical computing device measurements. Nonlinear methods disclosed herein may include neural networks as a platform to invert synthetic or virtual sensor responses of an optical tool. The inversion model is trained with sensing signals generated from multiple sensor elements and the fluid spectroscopy measurements in standard Optical-PVT databases.

The output of a nonlinear model as disclosed herein may include an averaged transmittance in each one of a plurality of specified wavelength bands of interest over a fluid spectrum. In some embodiments, the output of a nonlinear model may include a high-resolution transmittance as a continuous function of wavelength. In yet other embodiments, a nonlinear model transforms broadband filter responses originated from a principal components analysis (PCA) of a spectroscopy database to recover a high-resolution spectrum. Some embodiments provide spectral coverage of a recovered high-resolution spectrum in a spectral band where the optical computing device lacks sensing elements through cross-sensor optical data transformation. As a ruggedized spectral reconstruction technique, some embodiments provide additional spectral capabilities to any optical computing device configured for a specific optical fluid characterization.

In some embodiments, a full-range optical fluid spectroscopy is self-correlated. Accordingly, transmittance values at a particular wavelength can be estimated from the transmittance values at its vicinal and distant wavelengths. Data correlation can be determined through machine learning by using synthetic optical computing device responses of well-covered broad-band and narrow-band filters as inputs and the spectral transmittance of interest as output. This is in addition to using data information involving convolution portions of a spectrum. Some nonlinear models disclosed herein may use more-than-needed filter responses as candidate inputs to auto-select relevant information for nonlinear spectrum re-construction (e.g., in the VIS range), thus compensating for manufacturing variability of optical computing devices as disclosed herein.

As used herein, the term "electromagnetic radiation" refers to radio waves, microwave radiation, mid-infrared (MIR, from about 2500 nm to about 10000 nm) and near-infrared radiation (NIR, from about 750 nm to about 2500 nm), visible light (VIS, from about 400 nm to about 750 nm), ultraviolet light (UV, from about 200 nm to about 400 nm), X-ray radiation and gamma ray radiation.

Sensing elements described herein may include an element that optically interacts with a substance to determine quantitative and/or qualitative values of one or more physical or chemical properties of the substance. The sensing element may include multilayered interference elements designed to operate over a continuum of wavelengths in the electromagnetic spectrum from the UV region to the MIR region, or any sub-set of that region, including the VIS region and the NFR region. Electromagnetic radiation that optically interacts with the sensing element is modified to be readable by a detector such that an output of the detector can be correlated to the physical or chemical property or "characteristic" of the substance being analyzed.

As used herein, the term "characteristic" refers to a chemical, mechanical, or physical property of a substance. A characteristic of a substance may include a quantitative or qualitative value of one or more chemical constituents or compounds present therein, or any physical property associated therewith. Such chemical constituents and compounds may be referred to herein as "analytes." Illustrative characteristics of a substance that can be monitored with the optical computing devices described herein can include chemical composition (e.g., identity and concentration in total or of individual components), phase presence (e.g., gas, oil, water, etc.), impurity content, ion content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "optical computing device" refers to an optical device that is configured to receive an input of electromagnetic radiation, to interact the electromagnetic radiation with a substance and to produce an output of electromagnetic radiation from a processing (sensing) element arranged within the optical computing device. In some embodiments, an optical computing device also includes a detector to generate an electronic signal indicative of a characteristic of the substance. The optical computing device may include a sensing element, such as an integrated computational element (ICE), alternately referred to as a multivariate optical element (MOE), a narrow bandpass filter, or a broadband filter. The electromagnetic radiation that optically interacts with the sensing element is modified so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device, as well as other considerations known to those skilled in the art. In addition, emission and/or scattering of the fluid, for example via fluorescence, luminescence, Raman, Mie, and/or Raleigh scattering, can also be monitored by the optical computing devices described herein.

As used herein, the term "optically interact" or variations thereof refers to the reflection, transmission, scattering, diffraction, or absorption of electromagnetic radiation either on, through or from one or more sensing elements (i.e., ICE components, dielectric filters, narrow band filters, broad band filters, prisms, diffractive gratings, and the like) or a substance being analyzed by the sensing elements. Accordingly, optically interacted light refers to electromagnetic radiation that has been reflected, transmitted, scattered, diffracted, or absorbed, emitted, or re-radiated, for example, using a processing element, but may also apply to interaction with a substance.

This disclosure is related to methods of designing and implementing downhole optical computing devices using optical compressive sensing principles to recover a high-resolution spectrum. Methods of spectral reconstruction using such optical computing devices are also disclosed. Compressive sensing enables the optical computing devices disclosed herein to recover high-resolution spectra by measuring optical signals from downhole samples. The recovered high-resolution spectra enable determination of many properties of interest (e.g., characteristics) of the samples, including density, viscosity, chemical compositions, and gas-to-oil ratio, among others.

Optical techniques, such as absorption, vibrational and fluorescence spectroscopy, play an important role in real-time quantitative and qualitative chemical composition measurements in the oil and gas industry. Downhole optical fluid analysis methods as disclosed herein combine optical techniques and chemometrics to obtain key chemical composition information about a reservoir fluid. Compositional variation, compartmentalization and connectivity of a reservoir fluid can be established through downhole optical fluid analysis. Downhole optical computing devices as disclosed herein also play an important role in determining the level of drilling fluid filtrate contamination during reservoir fluid sampling process. Most conventional optical spectrometers are based on measuring separated spectral components through spectral energy separating optical devices such as narrow band filters, prisms or diffractive gratings. Each wavelength region is measured through different filters or different angle/location of dispersive optical device. The methods and systems disclosed herein use broadband thin-film optical filters, a light source and a single detector or an array of detectors to construct a compressive sensing spectrometer, which enables spectral measurement of a sample.

In a first embodiment, a system includes an optical computing device having an optical multiplexer that receives a sample light generated by an optical interaction between a sample and an illumination light, at least two sensing elements that optically interact with the sample light to generate at least a first modified light and a second modified light, wherein each of the first and second modified lights includes a first spectral band and a second spectral band, and a detector that measures a property of the first and second modified lights separately to generate a first signal and a second signal, respectively. The system may also include a controller including a processor and a memory, wherein the processor receives the first and the second signals and determines a spectral data value of the sample light, the spectral data value having a higher resolution than the first and second spectral bands.

In a second embodiment, a method includes obtaining a plurality of sensing signals with an optical computing device, each sensing signal being associated with a modified light generated from a sample light optically interacting with a sensing element in the optical computing device, and obtaining a plurality of synthetic responses using a sensing matrix and a sparse dictionary including a plurality of preselected basis functions associated with a plurality of sparse coefficients in a sparse vector. The method may further include adjusting the plurality of sparse coefficients by matching the plurality of sensing signals with the plurality of synthetic responses, and forming a spectrum using the plurality of sparse coefficients and the plurality of basis functions in the sparse dictionary.

In yet another embodiment, a method includes selecting full-range spectral data from a spectroscopy database associated to a sample and generating a plurality of synthetic sensor responses from the full-range spectral data to form a plurality of candidate training inputs. The method may also include selecting band-specific sample spectra as training targets for a spectrum reconstruction, building an input-dependent neural network inversion model with a machine learning procedure, forming a cross-band and variable input neural-network ensemble for spectrum determination, and implementing an ensemble inversion model on the optical computing device for real-time formation sampling and testing.

Figure 1B:
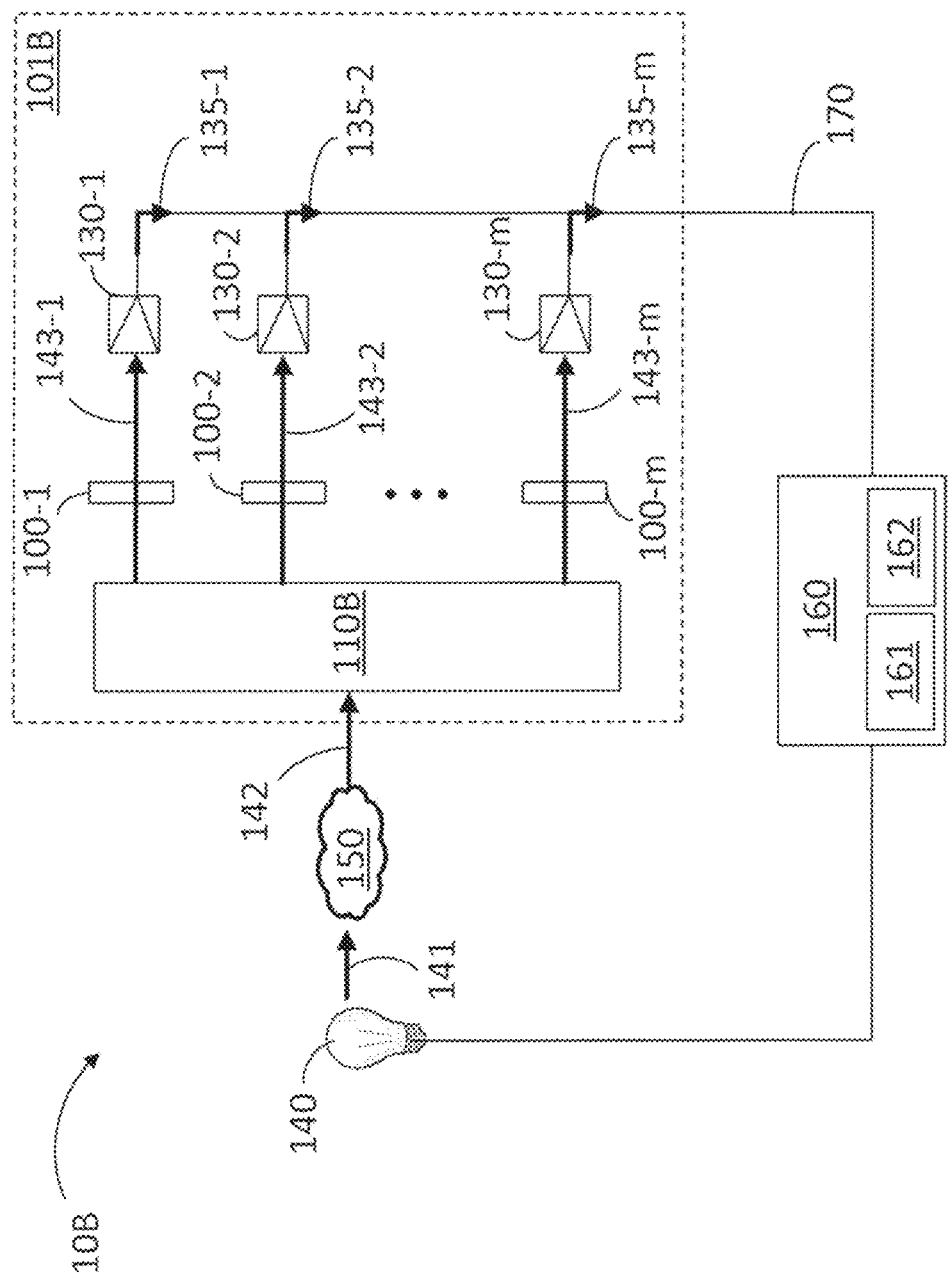

FIGS. 1A and 1B illustrate systems 10A and 10B, respectively, used for obtaining high-resolution spectral data of a formation fluid 150. Systems 10A and 10B are compact, high-resolution optical spectrometers that take advantage of compressive sensing as disclosed herein. Systems 10A,B each include a light source 140, and an optical computing device 101A and 101B, respectively (hereinafter, collectively referred to as optical computing devices 101). Light source 140 generates an illumination light 141 conveyed to interact with formation fluid 150 (i.e., the 'sample'), thus generating a sample light 142. Light source 140 may be a broadband lamp with a tungsten light bulb, a laser, a light-emitting diode, or any other source of electromagnetic radiation. In some embodiments, sample light 142 may include fluorescence emitted photons or Raman shifted photons derived from formation fluid 150.

Each optical computing device 101 includes an optical multiplexer 110A and 110B (hereinafter collectively referred to as optical multiplexers 110), a plurality of 'n' sensing elements 100-1 through 100-$n$ (hereinafter collectively referred to as sensing elements 100), and at least one detector 130 (e.g., detectors 130-1 through 130-$n$, cf. FIG.

1B). Optical multiplexers 110 separate sample light 142 into a plurality of beams of modified light 143-1 through 143-n (hereinafter collectively referred to as modified lights 143). Optical multiplexers 110 may include a free-space, waveguide, or fiber-optic based multiplexer, without limitation. In some embodiments, at least one of optical multiplexers 110 includes a beamsplitter, a lens, an arrayed waveguide grating, or any combination of the above.

Optical multiplexer 110A of FIG. 1A may include a rotating wheel having sensing elements 100 angularly spaced from each other (e.g., placed radially) on the plane of the wheel. The wheel rotates about an axis 120 that is parallel to the optical train coupling light source 140 with detector 130. As the wheel rotates, multiplexer 110A separates each of modified lights 143 in time, so that sensing signals 135 form a trace of pulses along a transmission line 170 to a controller 160.

In contrast, optical multiplexer 110B of FIG. 1B may be configured to spatially separate sample light 142 into portions directed separately and simultaneously to each of sensing elements 100. Accordingly, a plurality of detectors 130-1, 130-2, ..., 130-n (collectively referred hereinafter to as detectors 130) forms sensing signals from modified lights 143-1, 143-2, ..., 143-n (hereinafter collectively referred to as modified lights 143), respectively. Sensing signals 135 reach controller 160 through the transmission line 170 coupling detectors 130 with controller 160.

Sensing elements 100 interact with portions of sample light 142 to provide modified lights 143. A property of modified lights 143 may include an intensity indicative of a spectral density distribution of sample light 142. The spectral density distribution of sample light 142 may, in turn, be associated with chemical and physical properties of formation fluid 150. In some embodiments, an additional property of modified lights 143 indicative of chemical or physical properties of formation fluid 150 may include an intensity, a polarization state, a phase, a wavelength, or any combination of the above. Detectors 130 receive modified lights 143-1, 143-2, through 143-n, respectively. Detectors 130 provide sensing signals 135, which may be associated with the spectral density distribution of sample light 142 in a linear or a nonlinear manner.

In some embodiments, one or more of sensing elements 100 may include a multilayered dielectric broadband filter, each having a pre-selected transmission spectrum in a spectral band. The transmission spectra of sensing elements 100 is pre-selected according to a model that transforms sensing signals 135 into a spectral data value indicative of a high-resolution spectrum of sample light 142. In a compressive measurement as disclosed herein, the spectral data value of the sample light may have a higher resolution than the spectral band of any one of sensing elements 100. In some embodiments, the model that transforms sensing signals 135 into a spectral data value of sample light 142 may include any one of a linear regression algorithm (e.g., principal component analysis), a nonlinear model such as a neural network model, or any combination of the above, including a plurality (i.e., 'ensemble') of neural network models.

Transmission line 170 transmits response signals 135 to controller 160 for data processing. Transmission line 170 may be an electrical wire, an optical fiber, a radio-frequency wireless communication line or another type of wireless communication means for transmitting electromagnetic signals. In some embodiments, transmission line 170 may be an acoustic line configured to propagate sound pulses through a wellbore fluid. Controller 160 may include a processor 161 and a memory 162. Memory 162 stores data and commands which, when executed by processor 161, cause controller 160 to direct systems 10A,B to perform steps in methods consistent with the present disclosure. For example, upon execution by processor 161 of commands in memory 162, controller 160 may process response signals 135 and determine a high-resolution spectroscopic data value from sample light 142. Controller 160 may also communicate with light source 140 to control or modify illumination light 141.

Figure 2:
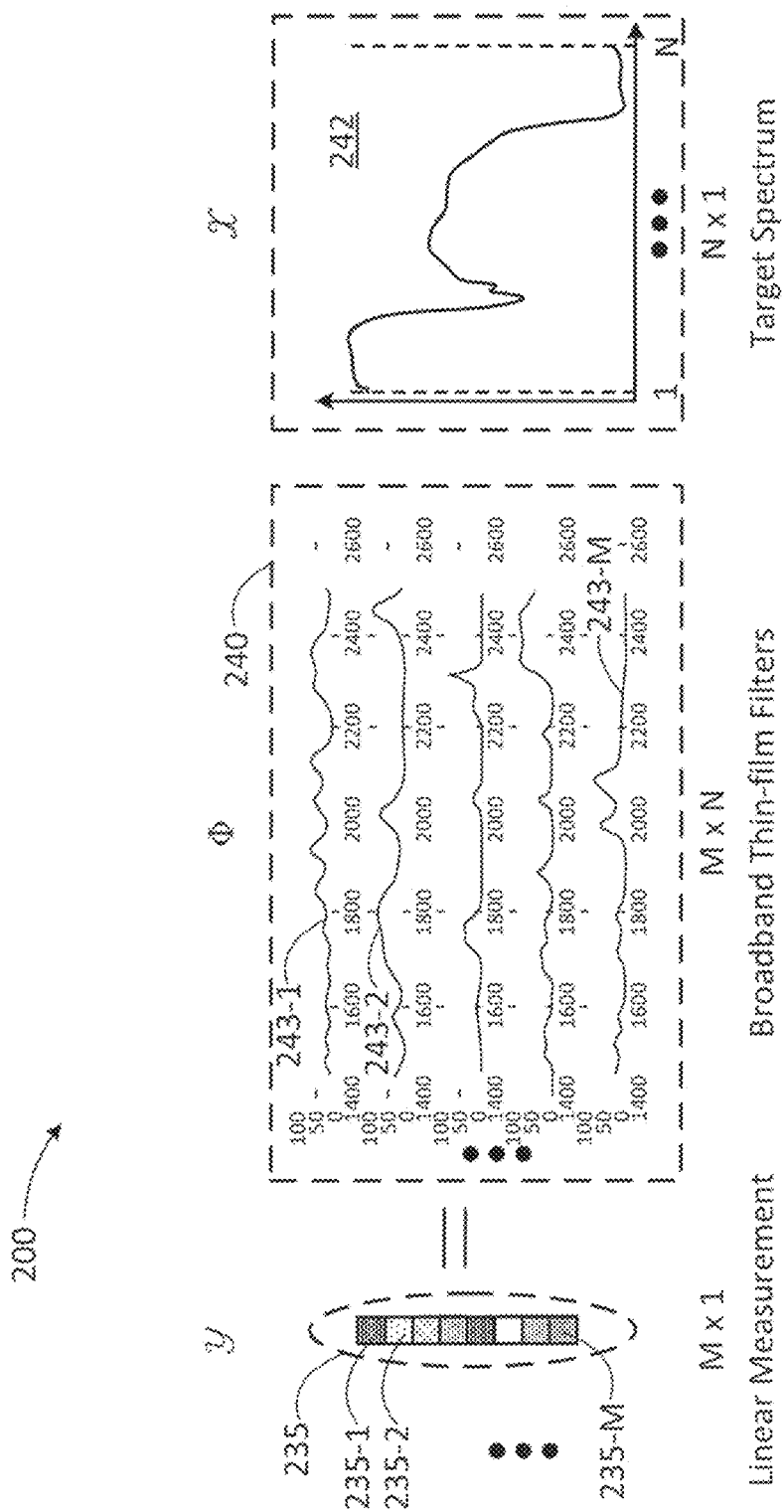
FIG. 2 is a block diagram of a compressive sensing measurement for obtaining high-resolution spectral data of a formation fluid from a plurality of optical computing device values.

FIG. 2 is a block diagram of a compressive measurement 200 for recovering high-resolution spectral data 242 of a formation fluid from a plurality of sensing signals 235-1, 235-2, ..., 235-M (hereinafter collectively referred to as sensing signals 235) collected from a sample (e.g., formation fluid 150, cf. FIGS. 1A, B). Sensing signals 235 (vector 'y') are mathematically represented as a linear transformation of a sample (target) spectrum 242 (vector 'x', having 'N' components) by a sensing matrix 240 ($\Phi$). Sensing matrix 240 includes rows 243-1, 243-2, ..., 243-M, each row corresponding to a plurality of broadband components (hereinafter collectively referred to as broadband components 243). Accordingly, sensing matrix 240 has dimensions 'M×N' ('M' rows×'N' columns) Broadband components 243 are illustrated as transmission spectra having the same resolution (i.e., number of elements, 'N') as sample (target) spectrum 242 ($x$).

Compressive sensing may be combined with, or used as, an alternative for the Shannon-Nyquist sampling framework. Embodiments disclosed herein use compressive sensing techniques to reconstruct sample spectrum 242 (having 'N' components) from the far fewer measurements in sensing signals 235 (having 'M' components). When sensing signals 235 are sparse and compressible as disclosed herein, the size of vector y is less, or even much less, than required by the Shannon-Nyquist sampling theorem. Accordingly, embodiments consistent with the present disclosure satisfy 'M<N' ('M' is less than 'N'), and in some embodiments 'M<<N' ('M' is much less than 'N'). In some embodiments, 'N' may be several hundred, such as 800 or even a thousand, while 'M' is a much smaller number, such as twenty, or ten, or even less (e.g., five or less).

As shown, compressive sensing measurement 200 can be described by the following linear matrix equation:

$$y = \Phi \cdot x \qquad (1)$$

Sample spectrum 242 belongs in an N-dimensional space ($x \in R^{N \times 1}$) and represents a spectrum of a sample having 'N' spectral bands (i.e., components). Given the spectral bandwidth of the measurement, the spectral resolution of the measurement is proportional to 'N' (the higher 'N', the better the spectral resolution of x). Sensing matrix 240 ($\Phi$) belongs in an M×N-dimensional space ($\Phi \in R^{M \times N}$). Compressive sensing techniques as disclosed herein solve Eq. 1 for a high-resolution spectrum x, given a vector y, of device values 135 (FIGS. 1A and 1B).

Spectral data 242 may be a high-resolution spectral decomposition of a sample light, broadband components 243 may be high-resolution transmittance spectra of each of a plurality of 'M' sensing elements, and device values 235 may include a plurality of sensing responses (e.g., sample light 142, sensing elements 100, and sensing responses 135, cf. FIG. 1).

Figure 3:
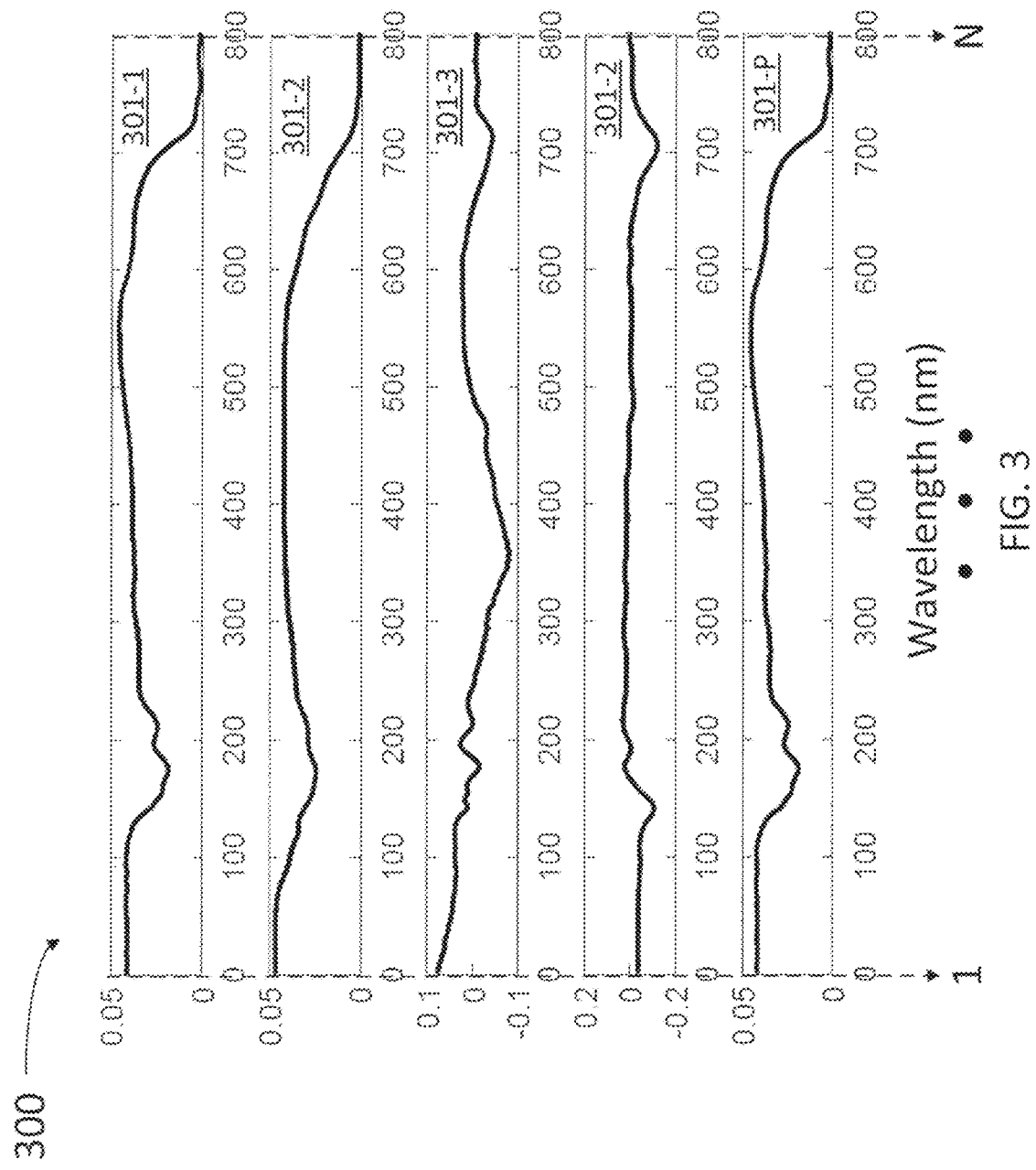
FIG. 3 illustrates a plurality of basis functions selected from a sparse dictionary for obtaining high-resolution spectral data of a formation fluid from an optical computing device.

FIG. 3 illustrates a plurality of basis functions 301-1, 301-2, ..., 301-P (hereinafter collectively referred to as basis functions 301) selected from a sparse dictionary 300 for obtaining high-resolution spectral data of a formation fluid from an optical computing device as disclosed herein. A sparse dictionary is a set of basis vectors or linear combination of basis vectors that can be used to represent spectra x. The high-resolution spectral data may be as sample spectrum 242 (cf. FIG. 2). For common samples found in many applications, sample spectrum 242 may not be sparse but it may be compressible. A sparse vector is understood as one in which a few components are non-zero. Accordingly, 'sparsity' of sample spectrum 242 may be defined as an integer parameter, K(x), indicating the number of non-zero components of vector x (cf. Eq. 1). Thus, vector x1 is more 'sparse' than vector x2, when K(x1)<K(x2). A sample spectrum 242 is said to be 'compressible' when the spectral profile, x, is sparse in a selected set of basis functions (e.g., basis functions 301).

In some embodiments, basis functions 301 may be selected from a principal component decomposition of a plurality of calibration spectra collected under different, controlled conditions comparable to sample spectrum 242. Accordingly, if sample spectrum 242 corresponds to a certain oil type and a parameter of interest is methane concentration, the calibration spectra may include a large number of samples of the same oil type injected with well known, varying methane concentrations including the methane concentrations expected in sample spectrum 242. Moreover, the parameter of interest may include a plurality of analyte concentrations and other physical properties of the same oil type, and the calibration samples may include a plurality of samples having well known values for each of the plurality of characteristics of interest. It is desirable that the calibration spectra be collected under laboratory conditions with a high-resolution spectrometer, or a "gold standard" such as an FTIR spectrometer. Calibration spectra thus obtained may be arranged as column vectors in a matrix, $x_{cal}$.

Mathematically, a compressive decomposition of high-resolution calibration spectra $x_{cal}$ in terms of basis functions 301 forming sparse dictionary 300 ($\Psi$) can be written as:

$$x_{cal} = \Psi \cdot \beta \quad (2)$$

where β is a matrix having columns that include 'sparse' coefficients applied to each of basis functions 301 in sparse dictionary 300 ($\Psi$); thus rendering each of calibration spectra $x_{cal}$. Given matrix $x_{cal}$ from high-resolution spectral measurements, Eq. 2 is solved to find matrices $\Psi$ and β. The solution is not unique, thus matrix $\Psi$ is selected according to a 'sparsity' constrain imposed on matrix β, as follows.

The sparsity constraint may be that each column $\beta_i$ in β has a number of non-zero elements less than or equal to a pre-selected integer value, K. This is formulated as the following optimization problem:

$$\arg \min \|x - \psi\beta\|^2 \; s.t. \|\beta_i\|_0 \; 0 \leq k \; \text{for} \; i = \{1, \ldots n\} \quad (3)$$

The optimization problem in Eq. 3 can be solved using a K-Singular Value Decomposition (KSVD) model. Without limitation, sparse dictionary 300 may include approximately 50 basis functions 301 for a calibration sample including one thousand spectra (i.e., $x_{cal}$ being a matrix with one thousand columns).

Figure 4:
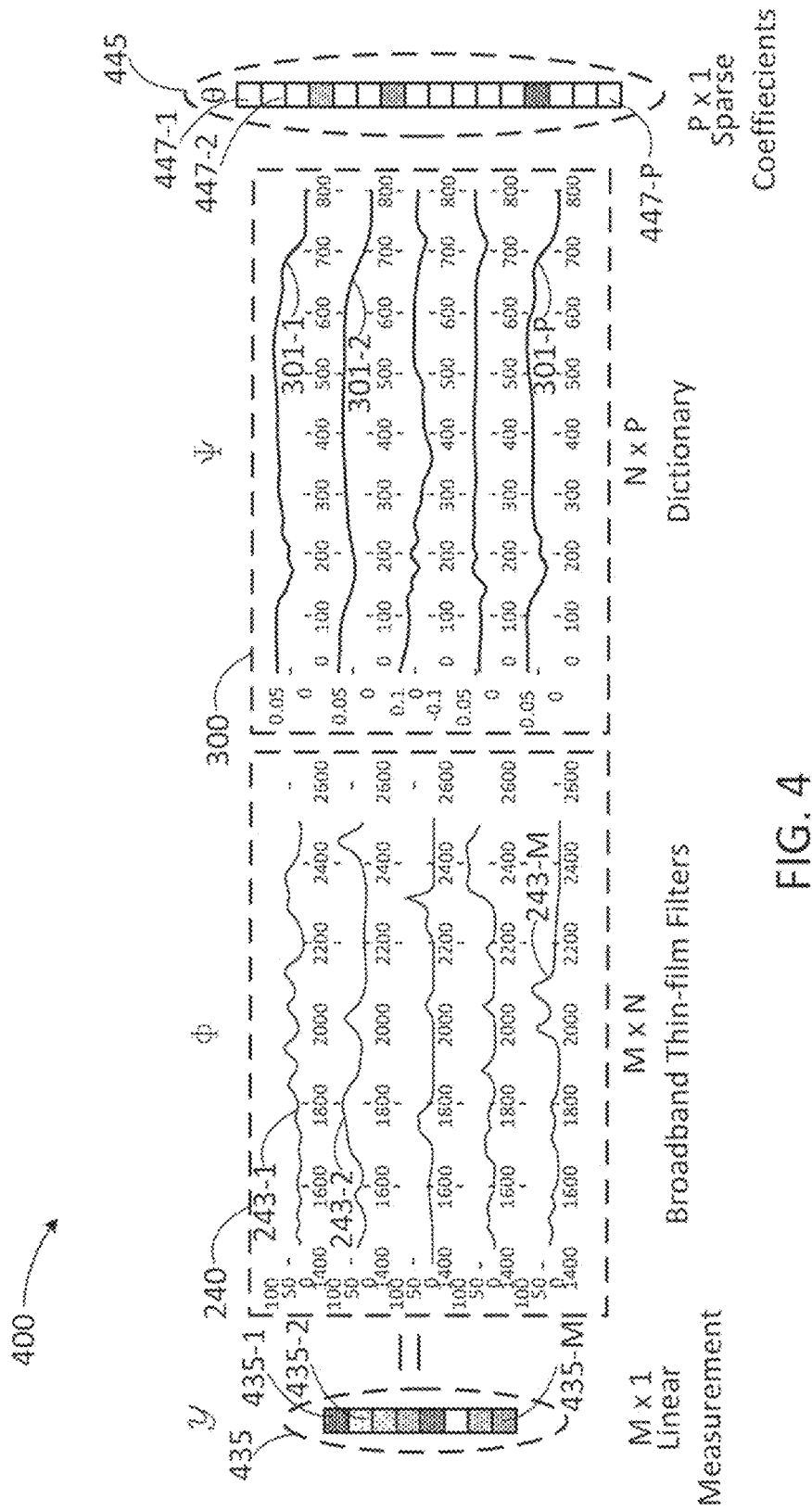
FIG. 4 is a block diagram of a compressive sensing measurement for obtaining high-resolution spectral data of a formation fluid from an optical computing device using the basis functions of FIG. 3 and sparse coefficients.

FIG. 4 is a block diagram of a compressive measurement 400 for obtaining high-resolution spectral data from a formation fluid with an optical computing device using basis functions 301 and a plurality of sparse coefficients 447 arranged in a sparse vector 445 (θ).

In compressed spectral representation, sample spectrum 242 can be represented by basis functions 301 in sparse dictionary 300. To render sample spectrum 242, basis functions 301 are weighted by sparse coefficients 447-1, 447-2, ..., 447-P (hereinafter collectively referred to as sparse coefficients 447).

From Eqs. 1 and 2, compressive measurement 400 can be expressed as $$y = \Phi \Psi \cdot \theta \quad (4)$$

Accordingly, when sensing signals 435-1, 435-2, ..., 435-M are collected with optical computing device 101, vector 435 ('y') is formed and Eq. 4 is solved for sparse vector 445, where matrices $\Phi$ (including broadband components 243) and $\Psi$ are known. Therefore, high-resolution sample spectrum 242 is recovered in analogy with Eq. 2 as:

$$x = \Psi \cdot \theta \quad (5)$$

Note that an advantage of solving Eq. 5 for sparse vector 445 as opposed to solving Eq. 1 directly for sample spectrum x is that the P-variables in sparse vector 445 (θ) may be fewer, or much fewer, than the N variables in high-resolution spectrum 242 (x). The high-resolution of spectrum x is recovered from Eq. 5 by the N-dimensional vectors in sparse dictionary 300 (matrix $\Psi$, there are 'P' of those vectors selected in Eq. 5). Furthermore, according to some embodiments sensing matrix $\Phi$ includes nonnegative values (as it is related to the transmittance of optical energy to a detector), while sparse dictionary matrix, $\Psi$, may include negative and positive elements associated with the same basis function.

Figure 5:
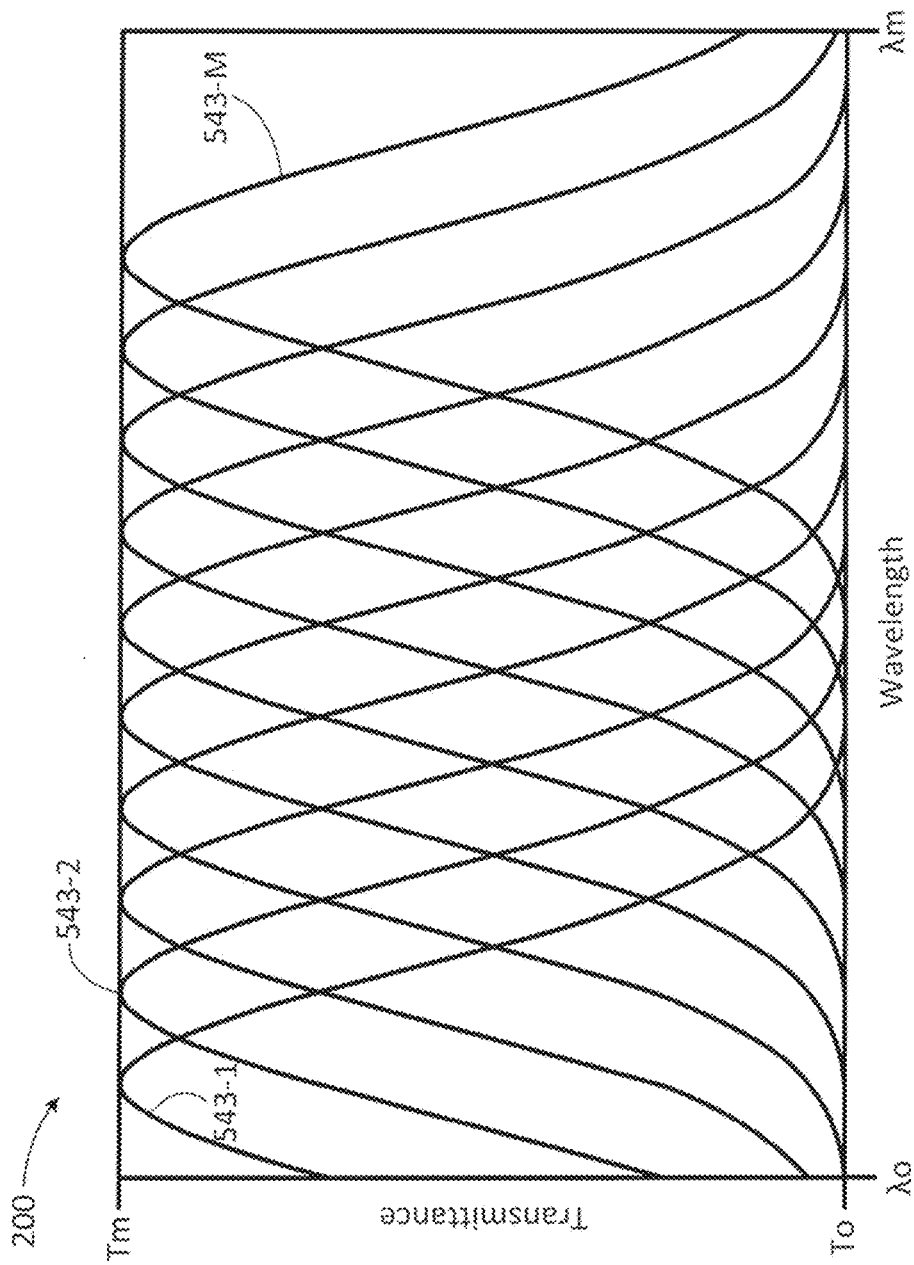
FIG. 5 illustrates a sensing matrix for use in an optical computing device to obtain high-resolution spectral data of a formation fluid.

FIG. 5 illustrates a sensing matrix 540 for use in an optical computing device to obtain high-resolution sample spectral data 242 (x). The sample may include a formation fluid present during oil and gas exploration and production operations, as disclosed herein. Sensing matrix 540 includes transmission spectra 543-1, 543-2, ..., 543-M (hereinafter collectively referred to as transmission spectra 543) from a plurality of 'M' sensing elements selected in an optical computing device as disclosed herein (e.g., sensing elements 100, optical computing devices 101A,B, and sensing matrix 240-$\Phi$-, cf. FIGS. 1A-B, 2 and Eq. 1).

Without limitation, the sensing elements for sensing matrix 540 include a set of Gaussian bandpass filters. Therefore, transmission spectra 543 are evenly distributed across the spectral wavelength of interest ($\lambda_0, \lambda_m$). One benefit of using an optical computing device as described by sensing matrix 540 is that manufacturing of sensing elements with transmission spectra 543 is relatively simple, with low manufacturing variability.

Figure 6:
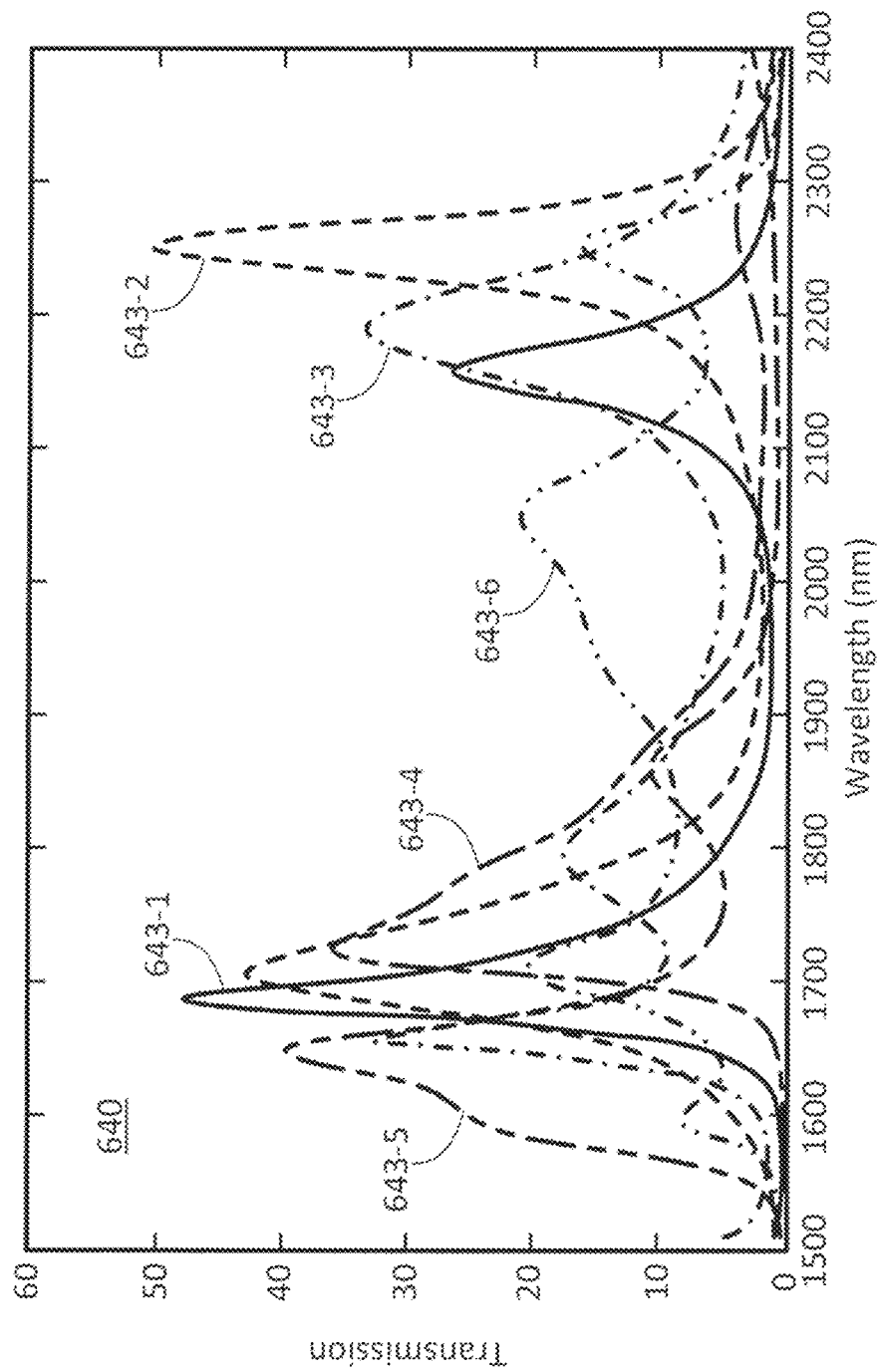
FIG. 6 illustrates transmission spectra from a plurality of sensing elements for use in an optical computing device to obtain high-resolution spectral data of a formation fluid.

FIG. 6 is a plot that illustrates transmission spectra 643-1, 643-2, ..., 643-6 (hereinafter collectively referred to as transmission spectra 643) from a plurality of sensing elements for use in a sensing matrix 640 (e.g., broadband components 243 in sensing matrix 240, and transmission spectra 543 in sensing matrix 540, cf. FIGS. 2 and 5). Transmission spectra 643 in sensing matrix 640 are selected according to a mutual coherence minimization procedure. Transmission spectra 643 can be selected to accommodate a sparse dictionary $\Psi$ according to a minimization rule. For example, the minimization rule may include reducing a mutual coherence (MC) between matrices $\Psi$ and $\Phi$. The mutual coherence may be defined using a matrix, D, or "effective dictionary," as follows:

$$D = [d_1 \; d_2 \; \ldots \; d_p] = \Psi^* \Phi \quad (6)$$

The mutual coherence, μ, is a measure of the 'overlap,' or 'inter-correlation' between the columns in matrix D defined as in Eq. 6. Mathematically, this may be expressed as:

$$\mu(D) = \mu(\Psi \cdot \Phi) = \max |\langle d_i, d_j \rangle|, \; i \neq j \quad (7)$$

Accordingly, spectral profile functions 643 in sensing matrix Φ are selected to minimize μ(D) in Eq. 7. Note that, in some embodiments, the mutual coherence minimization procedure in Eq. 7 is carried out with a known sparse dictionary Ψ. In fact, sparse dictionary Ψ may be obtained using the sparsity constrain method for the calibration spectra $x_{cal}$ (cf. Eqs. 2-3) and then sensing matrix Φ may be selected using Eq. 7.

Therefore, an optical computing device may obtain high-resolution spectral data of a formation fluid by fabricating sensing elements 100 having transmission spectra 643 (cf. FIGS. 1A-B). For example, one or more of sensing elements 100 may include an integrated computational element (ICE) or a thin film filter designed to provide any one of transmission spectra 643.

Figure 7:
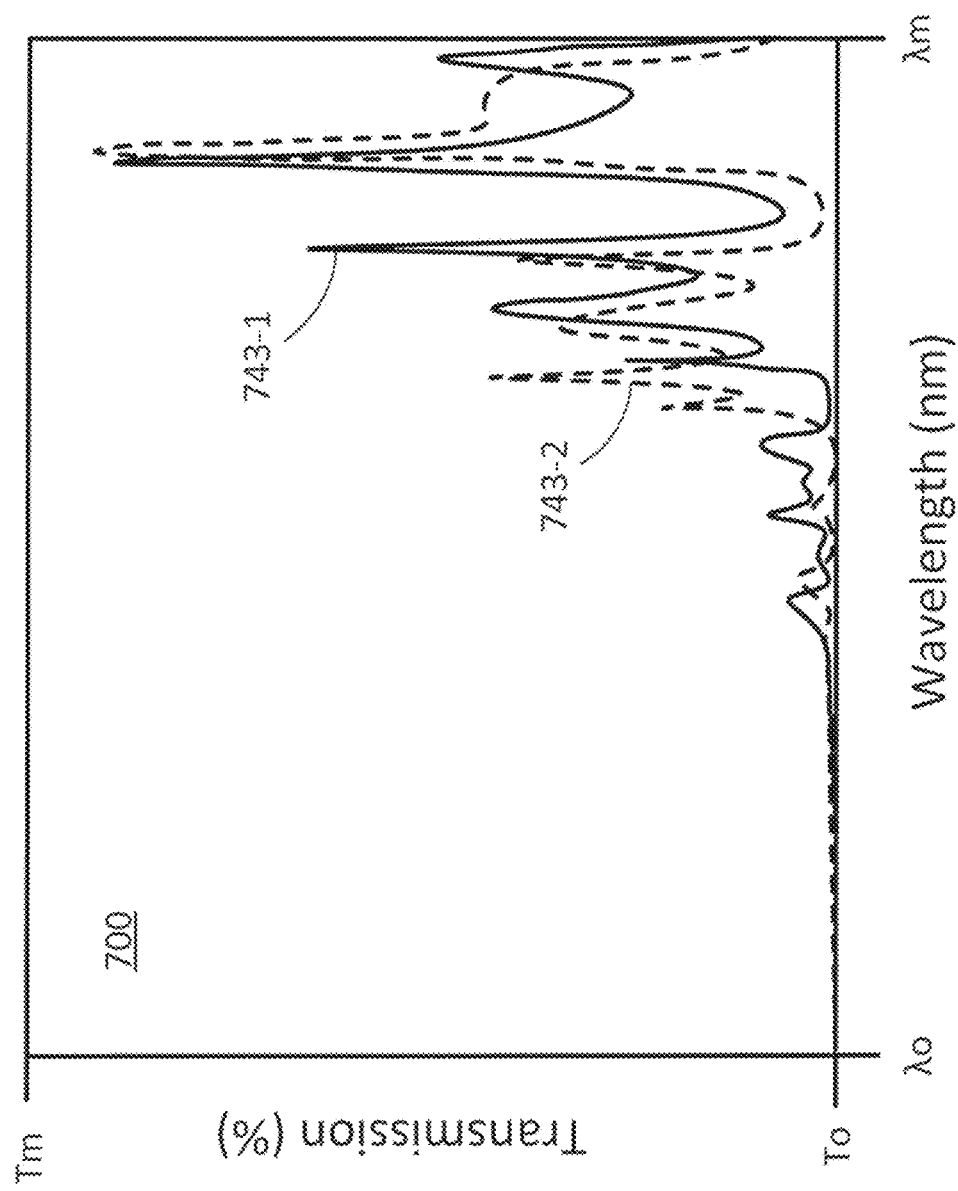
FIG. 7 illustrates transmission spectra from thin film filters for use as sensing elements in an optical computing device to obtain high-resolution spectral data of a formation fluid.

FIG. 7 illustrates transmission spectra 743-1 and 743-2 from thin film filters for use as sensing elements in an optical computing device to obtain high-resolution spectral data of a formation fluid. The fabrication of such sensing elements can be achieved by using thin-film optical filter fabrication techniques, such as Ion-assisted E-beam deposition, atomic layer deposition or magnetron sputtering deposition. Spectra 743-1 and 743-2 correspond to two thin film filters, each one having alternating layers of $SiO_2$ and Si material deposited on a glass substrate. The specific thicknesses of the different layers of material leading to spectra 743 are provided in TABLE I below.

TABLE I

| Layer # | Thickness (nm) | Thickness (nm) |
|---|---|---|
| 1 | 348.82 | 378.43 |
| 2 | 33.10 | 5.07 |
| 3 | 609.31 | 594.38 |
| 4 | 279.89 | 314.85 |
| 5 | 46.73 | 36.74 |
| 6 | 735.50 | 704.38 |
| 7 | 527.60 | 500.51 |
| 8 | 772.83 | 766.71 |
| 9 | 399.66 | 456.58 |
| 10 | 113.53 | 185.35 |
| 11 | 756.85 | 707.66 |

Although not necessarily the case, sensing elements 743 have the same number of alternating layers, each layer having comparable thickness between the two sensing elements.

Figure 8:
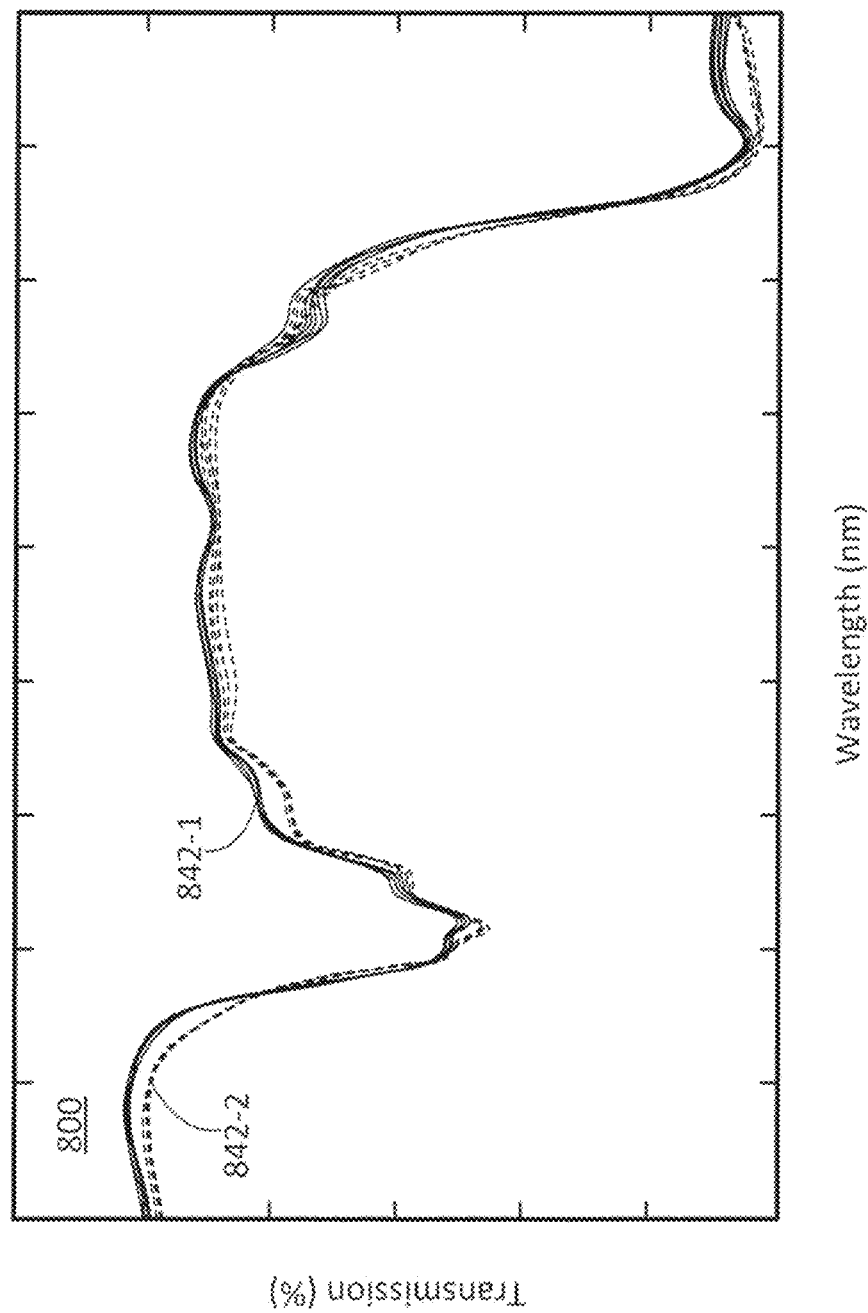
FIG. 8 is a chart illustrating a comparison between a high-resolution transmission spectra of a formation fluid reconstructed from optical computing device measurements using a linear method and a high-resolution transmission spectra of the formation fluid obtained with a high-resolution spectrograph.

FIG. 8 is a chart 800 illustrating a comparison between a high-resolution transmission spectra of a formation fluid 842-1, reconstructed from optical computing device measurements using a linear method, and a high-resolution transmission spectra of a formation fluid 842-2, obtained with a high-resolution spectrograph (i.e., the 'gold standard').

Spectra 842-1 are obtained by solving a compressive measurement minimization problem for a sparsity vector θ, given a set of sensing signals y provided by an optical computing device as disclosed herein (e.g., optical computing devices 101 and sparsity vector 445, cf. FIGS. 1A, B and 4). The optical computing device includes sensing elements associated with a sensing matrix Φ, and a set of pre-selected basis function forming a sparse dictionary Ψ of basis functions (e.g., sensing elements 100, sensing atrix 240, sparse dictionary 300, and basis functions 301, cf. FIGS. 1A-B, 2, and 3). Mathematically, this may be expressed as follows:

$$x_{opt} = \arg\min \|y - \Phi \cdot \Psi \cdot \theta\|_2^2 + \gamma \|\theta\|_1 \qquad (8)$$

The minimization model in Eq. 8 obtains an optimal sparse coefficient vector θ subject to a constraint for the amplitude of the solution to Eq. 8 (associated with an arbitrary multiplier, γ). With sensing values 'y', a high-resolution reconstructed spectrum x in the set of spectra 842-1 is obtained analogously to Eq. 2, as:

$$x = \Psi \cdot \theta. \qquad (9)$$

Note that while the dimensions of 'y' may be relatively small (5, 10, or maybe 20), the dimensions of x may be relatively high (100, 200, 1000 or even more).

Figure 9:
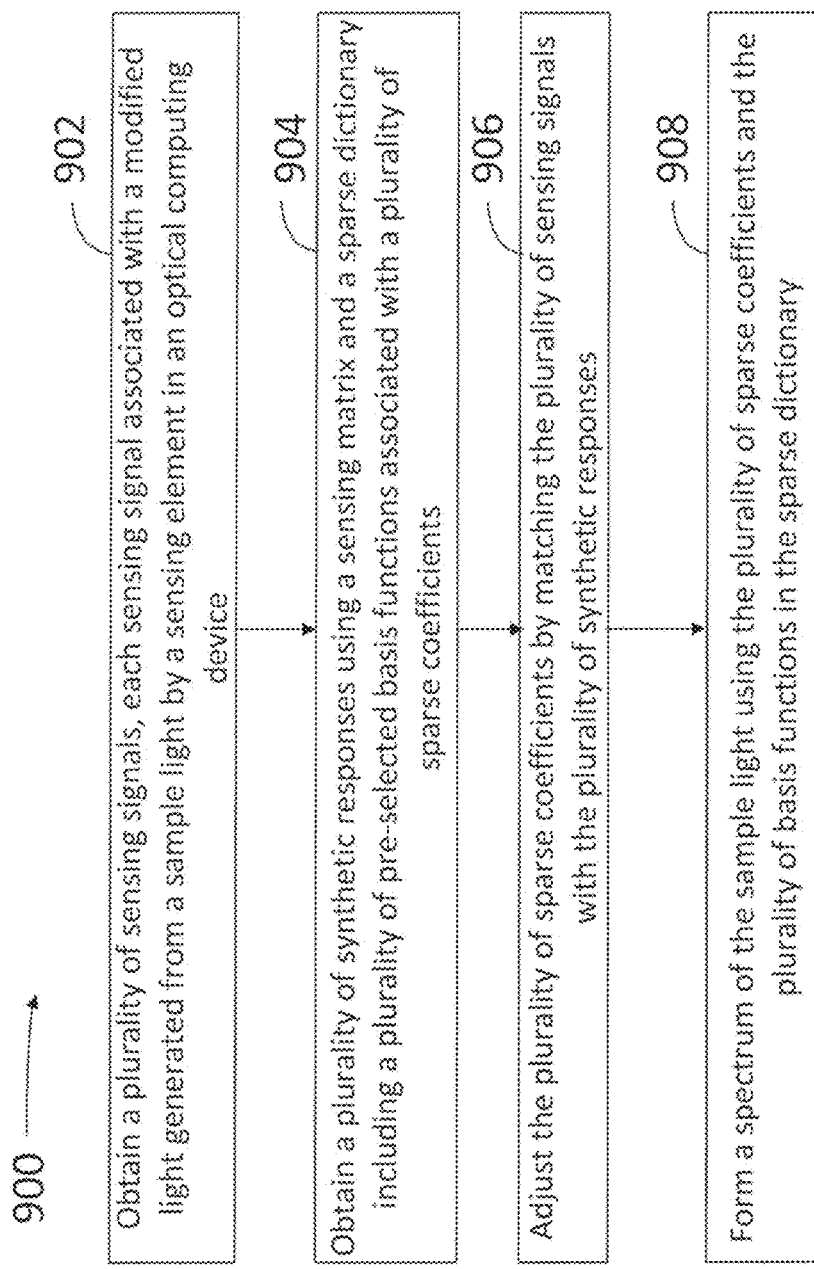
FIG. 9 illustrates a flow chart including steps in a linear method for obtaining high-resolution spectral data of a formation fluid with an optical computing device.

FIG. 9 illustrates a flow chart including steps in a linear method 900 for obtaining high-resolution spectral data of a formation fluid with an optical computing device. Method 900 may be performed at least partially by an optical computing device including a plurality of sensing elements (e.g., optical computing devices 101 and sensing elements 100, cf. FIGS. 1A-B). Steps in method 900 may be performed with a controller having a processor and a memory (e.g., controller 160, processor 161 and memory 162, cf. FIGS. 1A and B). The controller may perform at least some of the steps in method 900 when the processor executes commands stored in the memory. Moreover, the memory may store a sensing matrix and a sparse dictionary (e.g., sensing matrix 240 and sparse dictionary 300, cf. FIGS. 2 and 3). Methods consistent with the present disclosure may include at least some, but not all of the steps illustrated in method 900, performed in a different sequence. Furthermore, methods consistent with the present disclosure may include at least two or more steps as in method 900 performed overlapping in time, or almost simultaneously.

The memory may store a sensing matrix, Φ, and a sparse dictionary, Ψ (e.g., sensing matrix 240, and spare dictionary 300, cf. FIGS. 2 and 3). In some embodiments, sparse dictionary, Ψ, includes a plurality of basis functions associated with a desired characteristic of a sample (e.g., basis functions 301, cf. FIG. 3). Sensing matrix, Φ, may include a plurality of sensing element transmission functions (e.g., transmission functions 243). The plurality of sensing element transmission functions may include a Gaussian filter transmission function selected in view of cost, manufacturability, and bandwidth of operation or a transmission function selected according to a mutual coherence minimization model, or a transmission function from an optical thin film array (e.g., transmission functions 243, 543, and 643, cf. FIGS. 2, 5 and 6).

Step 902 includes obtaining a plurality of sensing signals, each sensing signal associated with a modified light generated from a sample light by the sensing element in an optical computing device.

Step 904 includes obtaining a plurality of synthetic responses using a sensing matrix and a sparse dictionary including the plurality of preselected basis functions associated with a plurality of sparse coefficients in a sparse vector. In some embodiments, step 904 includes forming a vector of synthetic responses by multiplying matrix Φ with matrix Ψ and a randomly selected vector of sparse coefficients, θ.

Step 906 includes adjusting the plurality of sparse coefficients by matching the plurality of sensing signals with the plurality of synthetic responses. In some embodiments, step 906 includes the added condition that the sparse vector has a bounded amplitude.

Step 908 includes forming a spectrum of the sample light using the sparse coefficients and the plurality of basis functions in the sparse dictionary. In some embodiments, step 908 may include forming a high-resolution spectrum closely resembling a spectrum of the sample light collected with a high-resolution spectrometer in the laboratory.

Figure 10:
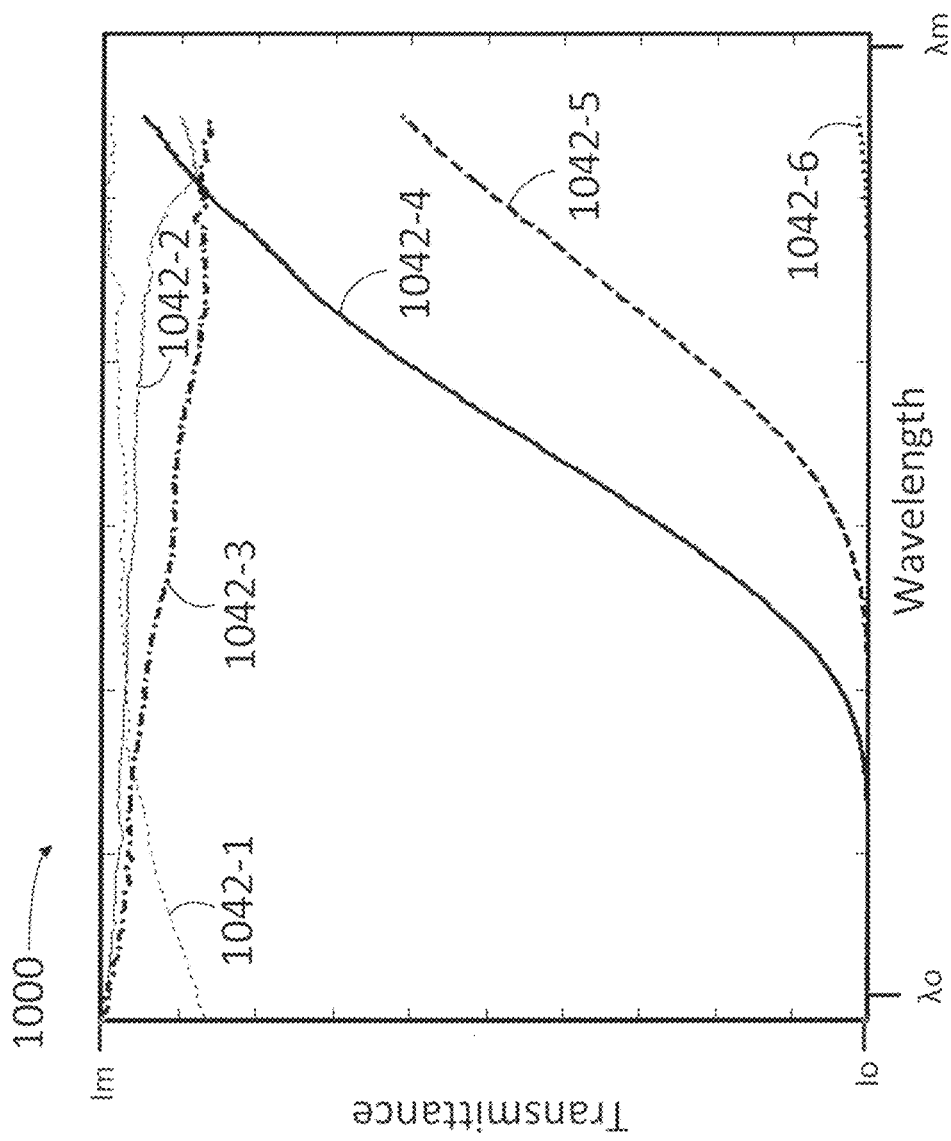
FIG. 10 is a chart illustrating transmittance spectra from a plurality of formation fluids.

FIG. 10 is a chart 1000 illustrating transmittance spectra 1042-1, 1042-2, . . . , 1042-6 (hereinafter collectively referred to as spectra 1042) from a plurality of formation fluids of interest in the oil and gas industry. Chart 1000 includes wavelength values in the abscissae (arbitrary units) covering a spectral range given by ($\lambda_0$, $\lambda_m$). Chart 1000 also includes transmittance values in the ordinates (arbitrary units), covering a range given by ($I_0$, $I_m$). Spectrum 1042-1 corresponds to a gas example, spectrum 1042-3 corresponds to a water example, and spectrum 1042-3 corresponds to a condensates example of formation fluids. Spectrum 1042-4 corresponds to a light oil, spectrum 1042-5 corresponds to a medium oil, and spectrum 1042-6 corresponds to a heavy oil.

Without limitation, the range covered by ($\lambda_0$, $\lambda_m$) may be any one of the UV, VIS, NIR, MIR, wavelength ranges, or a range outside any of the above. In some embodiments, it may be desirable to collect or reconstruct gaps of spectroscopic data that may occur in a database. For example, in some circumstances a high-resolution spectrum for a formation fluid may exist in the UV and the NIR, but the existing data in the VIS region may have lower resolution, or may be distorted, lost, or non-existent. Accordingly, it may be desirable to retrieve, recover, synchronize and corroborate data in a certain spectral region (e.g., the VIS region) using high-resolution data from at least one different spectral region.

More specifically, range ($\lambda_0$, $\lambda_m$) may include the VIS range. As shown in chart 1000, spectra 1042 show distinct spectral signatures that may be useful in the differentiation between formation fluids leading to each of the spectra. Therefore, estimating fluid color spectra at selected visible and/or NIR wavelength range has special interest in downhole fluid analysis. For example, VIS spectra can distinguish between light oil 1042-4, medium oil 1042-5, or heavy oil 1042-6. VIS spectrum patterns in chart 1000 can also distinguish between oil and gas condensates, or water, 1042-1, 1042-2 or 1042-3.

Nonlinear models consistent with the present disclosure include data from the NIR or MIR regions to improve or provide high-resolution spectral data in the VIS region (e.g., chart 1000). Without limitation, other combinations may be envisioned within the scope of the present disclosure, such as UV and VIS data input to a nonlinear model for providing high-resolution data in the NIR or MIR region. Nonlinear models used in the context of optical computing devices as disclosed may include nonnegative spectra of sensing elements (e.g., sensing elements 100, and sensing matrix 240, cf. FIGS. 1A-B, and 2) without limiting the solution space. Accordingly, a nonlinear model as disclosed herein may provide non-negative spectral output without constraining optical computing device hardware or solution quality. Furthermore, the quality of nonlinear transformations is weakly dependent on the fluid types used for downhole fluid analysis. This is due to the ability of nonlinear neural networks to make universal function approximation through machine learning with adequate training examples and structural complexity. This is also due to the ability of neural networks to correct distorted spectra through regularized training and to produce smoothed output in prediction even when sensor data is out of the calibration range.

Figure 11:
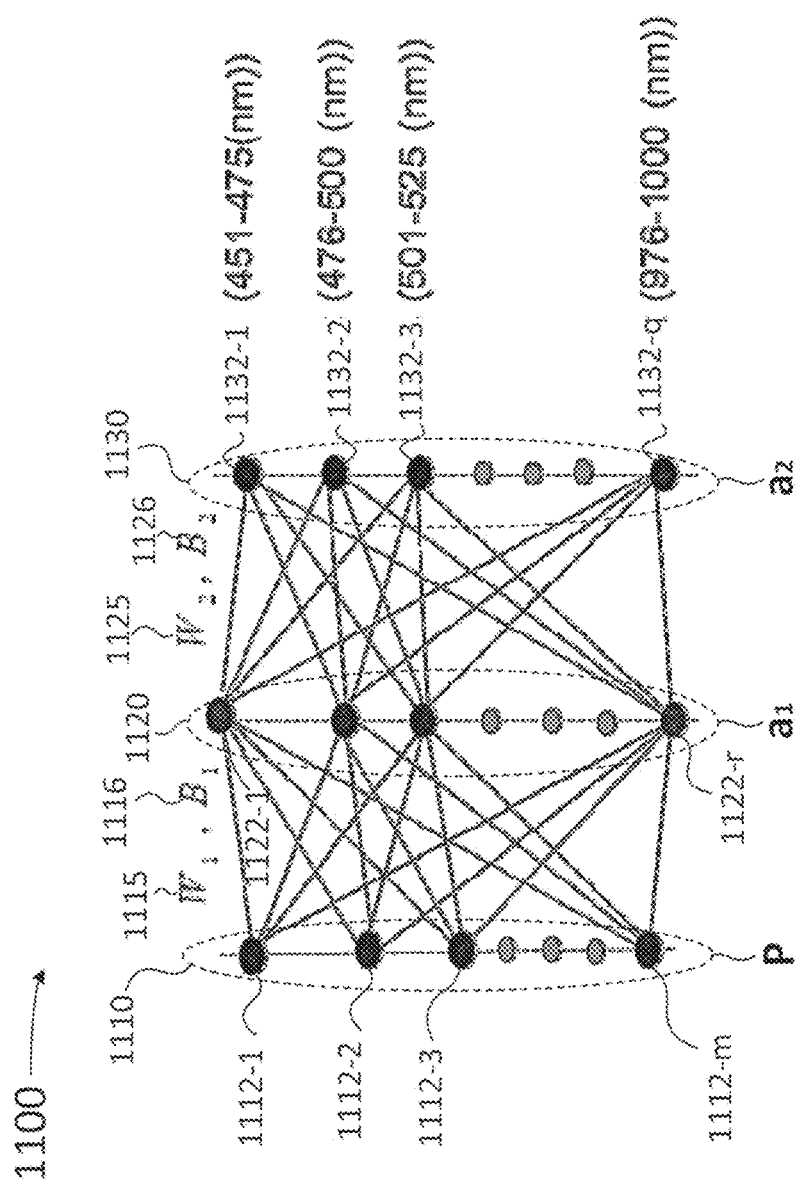
FIG. 11 illustrates a multi-input, multi-output (MIMO) neural network transformation for use in a nonlinear method for obtaining high-resolution spectral data of formation fluids from optical computing device measurements.

FIG. 11 illustrates a multi-input, multi-output (MIMO) neural network transformation structure 1100 for use in a nonlinear method to obtain high-resolution spectral data of formation fluids from optical computing device measurements. MIMO transformation 1100 includes input layer 1110 having input nodes 1112-1, 1112-2, . . . , 1112-$m$ (hereinafter collectively referred to as input nodes 1112). Intermediate hidden layer 1120 includes nodes 1122-1, 1122-2, . . . , 1122-$r$ (hereinafter collectively referred to as nodes 1122). Output layer 1130 includes output nodes 1132-1, 1132-2, . . . , 1132-$q$ (hereinafter collectively referred to as output nodes 1132). The number of input nodes 1112($m$), hidden nodes 1122($r$), and output nodes 1132($q$) may be different from one another, without limitation. For example, '$m$,' is associated with the number of sensing signals provided by the sensing elements in the optical computing device (e.g., sensing signals 135, sensing elements 100, and optical computing devices 101 in FIGS. 1A-B). The value of '$r$' may be more than '$m$,' or less than '$m$,' without limitation. Each one of input nodes 1112 receives a sensing signal $P_i$ from sensor element '$i$'. Sensing signals $P_i$ may form the components of a vector P indicating synthetic sensing responses of sensing elements in the optical computing device (e.g., sensing elements 100 in optical computing devices 101, cf. FIGS. 1A-B). Inputs 1112 ($P_i$) may also include measurement data from temperature, pressure and density sensors.

For input layer 1110, MIMO transformation 1100 uses a coefficient set 1115 ($W_1$, e.g., a matrix of size '$r \times m$'), and a vector set 1116 ($B_1$) of size '$r \times 1$' find '$r$' intermediate outputs $a_1$, using the '$m \times 1$' sensing values Pi as follows:

$$a_1 = f_1(\eta_1) = \frac{e^{\eta_1} - e^{-\eta_1}}{e^{\eta_1} + e^{-\eta_1}}, \eta_1 = W_1 \times P + B_1 \quad (10)$$

Each one of the r intermediate outputs $a_i$ is associated with an intermediate hidden node 1122. Transfer function $f_1$ in Eq. 10 is, without limitation, a hyperbolic tangent sigmoid function. For intermediate layer 1120, MIMO transformation 1100 uses coefficient set 1125 ($W_2$, e.g. a '$q \times r$' matrix) and vector set 1126 ($B_2$) of size '$q \times 1$' to find output functions $a_2$ $$a_2 = f_2(\eta_2) = \frac{e^{\eta_2} - e^{-\eta_2}}{e^{\eta_2} + e^{-\eta_2}}, \eta_2 = W_2 \times a_1 + B_2 \quad (11)$$

Coefficient sets $W_1$, $W_2$, $B_1$ and $B_2$ are estimated using a machine-learning algorithm. In MIMO transformation 1100, output nodes 1132 are associated with different regions of a sample light spectrum, 'x.' For example and without limitation, node 1132-1 may provide an average of 'x' along the spectral range from 451-475 nm. Node 1132-2 may provide an average of 'x' over the spectral range from 476-500 nm. Node 1132-3 may provide an average of 'x' over the spectral range from 501-525 nm, and node 1132-$q$ may provide an average of 'x' over the spectral range from 976-1000 nm.

Accordingly, output layer 1130 in MIMO transformation 1100 may include a visible spectrum ranging from 450 to 1000 nanometers binned such that each bin spans a 25 nm range. The assignment of the 'x' average for each given wavelength range is made in training data prior to model calibration. After MIMO transformation 1100 is built, each output 1132 indicates wavelength-specific transmittance based on the pre-assignment. Multi-bin outputs can be calculated simultaneously for best real-time data processing.

MIMO transformation 1100 as expressed in Eqs. 10-11 may reveal cross-band spectral data correlation from optical computing device measurements. For example, at least one of the input values, $P_i$, may correspond to a sensing element that has a transmission spectrum different from any of the spectral bands associated with output nodes 1132. Furthermore, Eqs. 10-11 may be used to obtain an inversion algorithm for robust real-time calculation of high-resolution visible spectra of different types of formation fluids by adjusting the wavelength ranges of output nodes 1132 during the machine learning process. The hyperbolic tangent sigmoid transfer functions in Eqs. 10-11 can also ensure non-negative spectrum during transient period of fluid sampling and testing. Accordingly, tangent sigmoid functions in Eqs. 10-11 provide a wide margin of variability in the output node values 1132 such that a positive definite value a2 for spectral average is guaranteed without imposing severe constraints to coefficients $W_1$, $W_2$, $B_1$ and $B_2$. This is especially desirable when a positive definite set of functions $a_2$ represents energy data.

Figure 12:
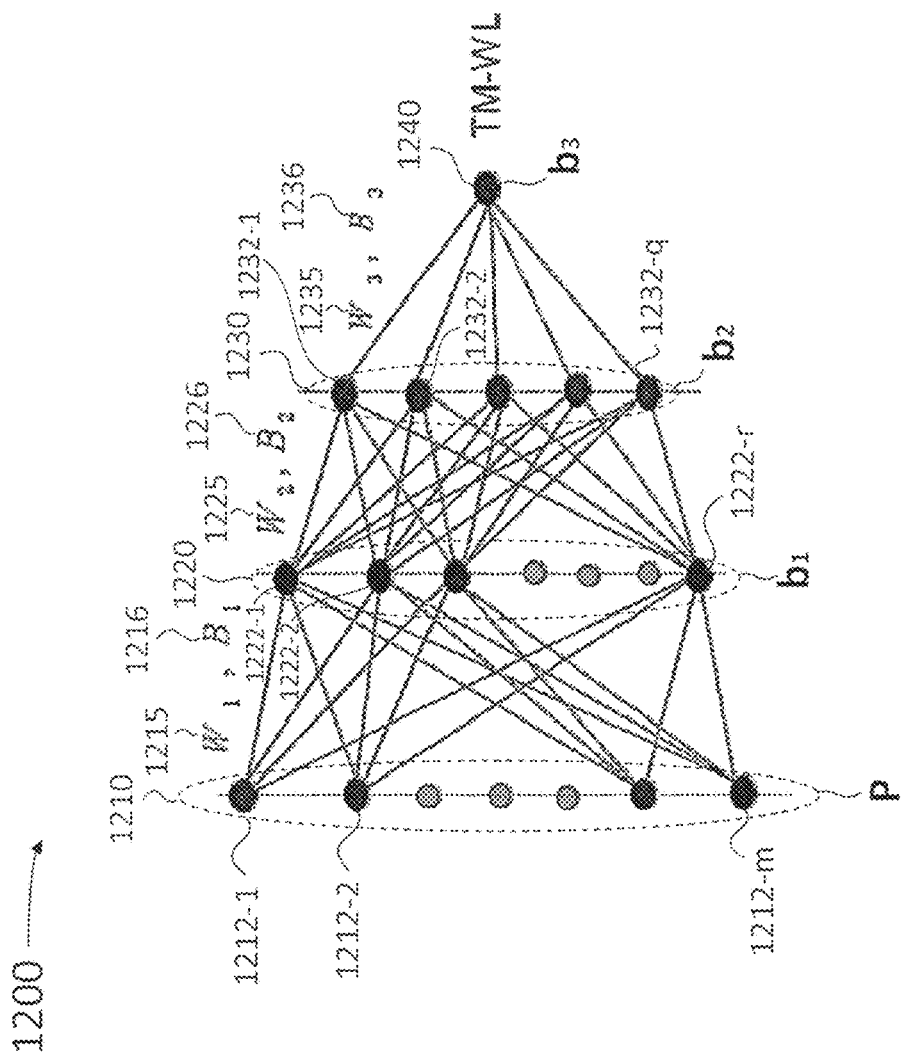
FIG. 12 illustrates a multi-input, single-output (MISO) neural network transformation for use in a nonlinear method for obtaining high-resolution spectral data of formation fluids from optical computing device measurements.

FIG. 12 illustrates a multi-input, single-output (MISO) transformation 1200 for use in a nonlinear method for obtaining high-resolution spectral data of formation fluids from optical computing device measurements, as disclosed herein (e.g., optical computing devices 101, cf. FIGS. 1A-B).

MISO transformation 1200 includes input layer 1210 having input nodes 1212-1, 1212-2, ..., 1212-m (hereinafter collectively referred to as input nodes 1212). Intermediate hidden layer 1220 includes nodes 1222-1, 1222-2, ..., 1222-r (hereinafter collectively referred to as nodes 1222). Intermediate hidden layer 1230 includes nodes 1232-1, 1232-2, ..., 1232-q (hereinafter collectively referred to as nodes 1232). The number of input nodes 1212(m), intermediate nodes 1222(r), and nodes 1232(q) may be different from one another, without limitation. A single output value 1240 provides a desired spectroscopic value indicative, for example, of a component of a high-resolution spectrum of the sample light at a selected wavelength. The values m, r and q are arbitrary, as in MIMO transformation 1100. Likewise, each one of input nodes 1212 receives a sensing signal $P_i$ from sensor element 'i'. Pi inputs 1212 may also include measurement data from temperature, pressure, and density sensors, and a wavelength. Value 1240 may be computed as a third function ($a_3$) of parameter sets 1235 ($W_3$, e.g., a 1×q-size vector) and 1236 ($B_3$, a single number), as follows.

$$a_3 = f_3(\eta_3) = \frac{e^{\eta_3} - e^{-\eta_3}}{e^{\eta_3} + e^{-\eta_3}}, \eta_3 = W_3 \times a_2 + B_3 \quad (12)$$

Eq. 12 estimates a high-resolution spectrum when the model is trained against calibration spectra using wavelength, λ, as one of the input parameters, $P_{m+1}$ (1212), in input layer 1210. For example, output node 1240 may be optical transmittance as an explicit function of wavelength (λ) and other candidate inputs (e.g., sensing signals 135, pressure and temperature, all included in input layer 1210).

To generate a high-resolution waveform of a VIS spectrum, for example, MISO transformation 1200 may be obtained by training the optical computing device with a measured spectrum (e.g., selected from calibration spectra $x_{cal}$, cf. Eq. 2) through the wavelength range (e.g., 450-1000 nm) step by step. At each step, coefficients 1215 ($W_1$), 1216 ($B_1$), 1225 ($W_2$), 1226 ($B_2$), 1235 ($W_3$), and 1236 ($B_3$) are adjusted according to a resulting transmittance for each wavelength, given that inputs 1212 remain unchanged (e.g., the sensing responses of the optical computing device and sample temperature and pressure are the same across a single high-resolution spectrum, x). The resolution of MISO transformation 1200 thus trained may be as high as the resolution of the collected spectrum used for calibration. A wavelength-dependent MISO transformation 1200 obtained as above is desirable when the fluid transmittance spectrum to be reconstructed has a sharp peak or feature, which may not be recovered by low-resolution re-construction.

Figure 13B:
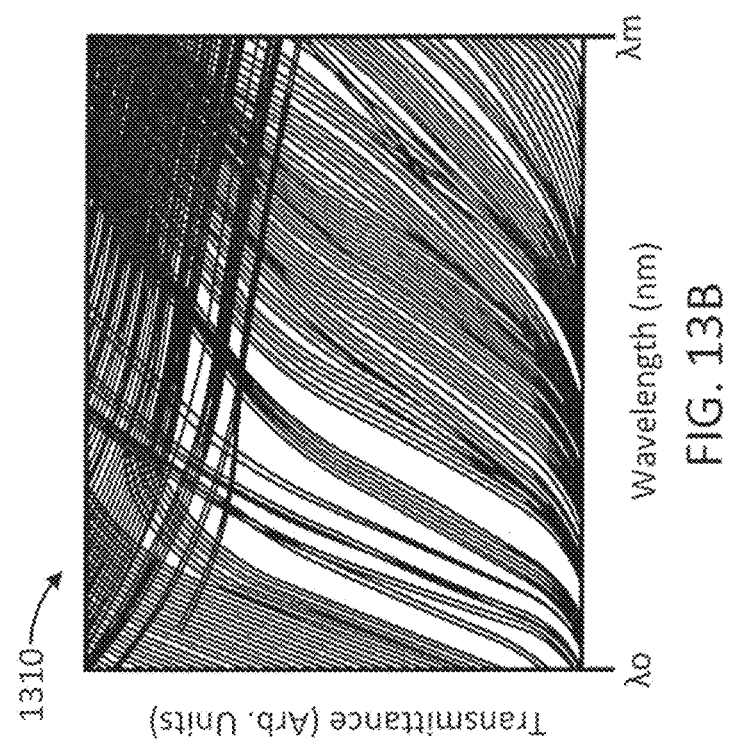
FIG. 13B illustrates raw transmittance spectra corresponding to the absorbance spectra of FIG. 13A.
Figure 13A:
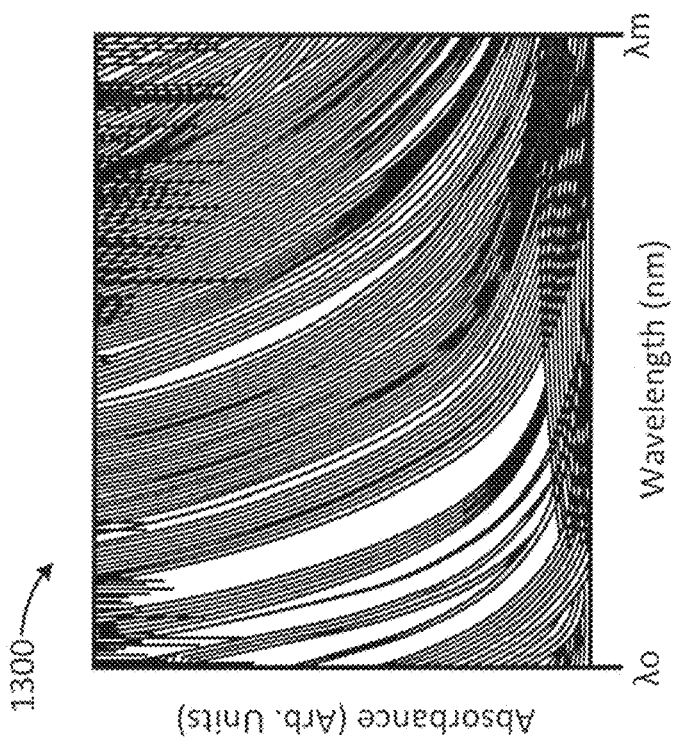
FIG. 13A illustrates raw absorbance spectra obtained from a plurality of formation fluids.

FIG. 13A illustrates raw absorbance spectra 1300 obtained from a plurality of formation fluids using a high-resolution FTIR spectrometer. The abscissae in FIG. 13A includes a wavelength region ($λ_0$, $λ_m$) that may be as described above (cf. FIG. 10), while the ordinates indicate an absorbance value (in arbitrary units). Spectra 1300 includes spectra from a visible absorbance spectral database measured on a variety of fluids including light oil, medium oil, heavy oil, gas condensates, gas and water under different temperatures and pressures. Spectra 1300 show the effect of noise for higher absorbance levels (the ordinate axis), due to the low signal to noise ratio received by the spectrometer when absorbance is high.

FIG. 13B illustrates raw transmittance spectra 1310 corresponding to the absorbance spectra 1300 of FIG. 13A (e.g., spectra 1042, cf. FIG. 10). Transmittance spectra 1310 inherits the noisy character of spectra 1300. The abscissae in FIG. 13B includes a wavelength region ($λ_0$, $λ_m$) that may be as described above (cf. FIG. 10), while the ordinates indicate a transmittance range (in arbitrary units) that may also be as described in FIG. 10.

In some embodiments, a Bayesian regularization training algorithm is used during machine learning to re-construct smooth transmittance spectra even when the original spectra are noisy (e.g., spectra 1300 and 1310). Bayesian regularization uses the concept of Bayesian statistics for smoothing noisy data and providing optimal predictions. The resulting nonlinear model is a probabilistic approach that maximizes the information content in the data set to overcome the limitation of a noisy measurement typically obtained with laboratory spectrometers. Methods consistent with this disclosure are capable of providing optimal solutions for database re-construction. Spectral data reconstructed as disclosed here have many applications for advanced modeling and fluid analysis.

FIG. 14A illustrates re-constructed transmittance spectra 1400 reconstructed from raw transmittance spectra 1310 in FIG. 13B using MISO transformation 1200.

FIG. 14B shows absorbance spectra 1410 converted from re-constructed transmittance spectra 1400 (cf. FIG. 14A). It can be observed that spectra 1400 and 1410 are smoother than original spectral measurements 1310 and 1300, respectively (cf. FIGS. 13A and 13B). Results in FIGS. 14A and 14B indicate that nonlinear machine learning with neural networks (e.g., MISO transformation 1200) provides robust and universal inversion models for optical fluid spectrum re-construction, applicable to different types of formation fluids. It is also possible to use a neural network re-constructed high-resolution visible and NIR spectral database for advanced modeling in predicting formation fluid compositions and properties.

The performance of optical computing device data deconvolution model consistent with the present disclosure is robust with respect to design and fabrication errors in sensor elements. MIMO or MISO models 1100 and 1200 can be calibrated using a variety of sensor configurations spanning multiple spectral regions providing suitable input signals $P_i$ (e.g., signals 1110 and 1210, cf. FIGS. 11 and 12).

Figure 15:
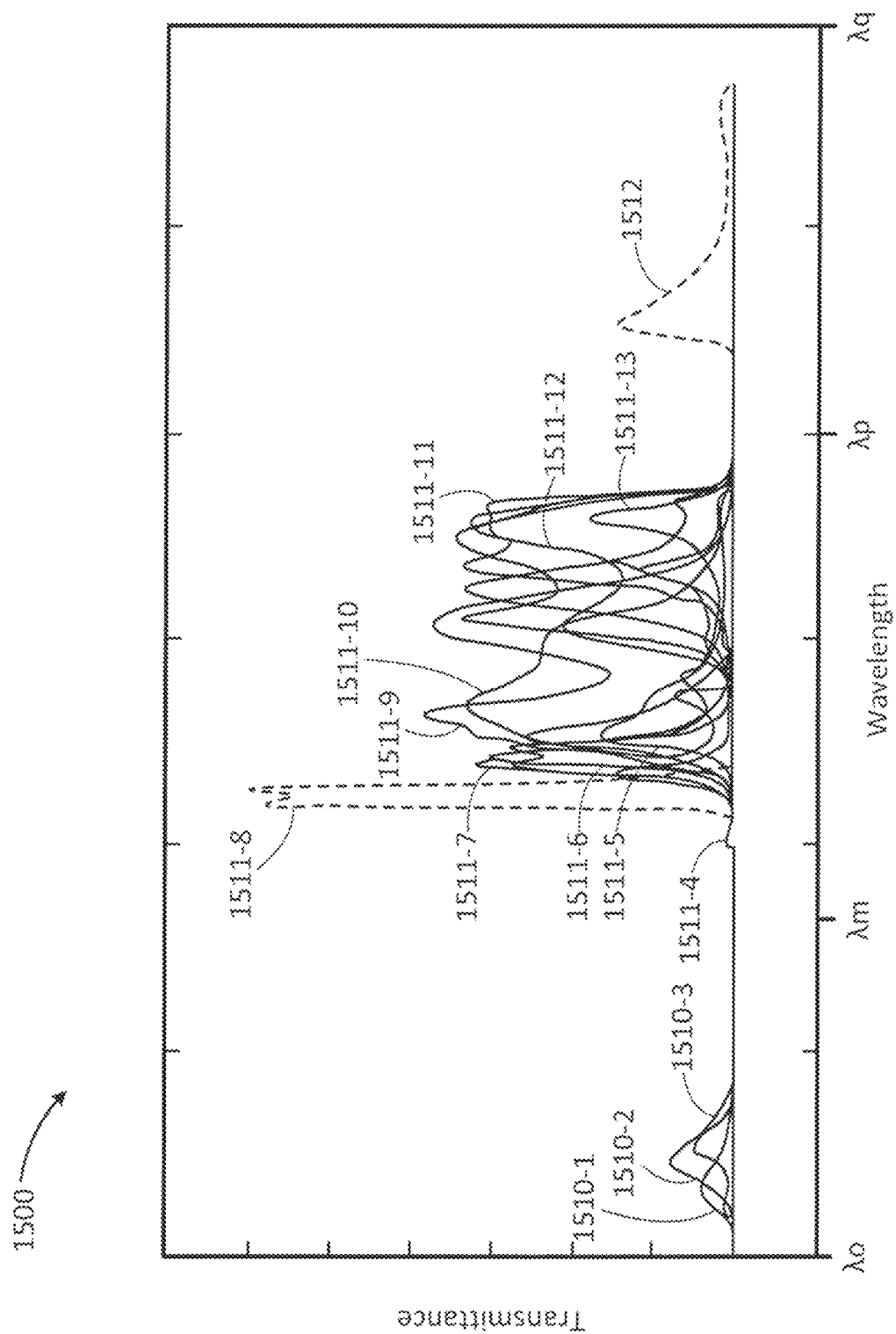
FIG. 15 is a plot illustrating transmittance spectra from a plurality of sensing elements for use in an optical computing device to obtain high-resolution spectral data of a formation fluid.

FIG. 15 is a plot 1500 illustrating transmittance spectra 1510-1, 1510-2, and 1510-3 (hereinafter collectively referred to as VIS spectra 1510), transmittance spectra 1511-1 through 1511-13 (hereinafter collectively referred to as NIR spectra 1511), and MIR transmittance spectrum 1512. VIS spectra 1510, NIR spectra 1511, and MIR spectrum 1512 correspond to a plurality of sensing elements for use in an optical computing device to obtain high-resolution spectral data of a formation fluid, as disclosed herein (e.g., sensing elements 100 and optical computing devices 101, cf. FIGS. 1A-B).

The abscissae in plot 1500 includes wavelength ranges ($\lambda$o, $\lambda$m), ($\lambda$m, $\lambda$p), and ($\lambda$p, $\lambda$q), wherein ($\lambda$o, $\lambda$m) belongs within the VIS wavelength range, ($\lambda$m, $\lambda$p) belongs within the NIR range, and ($\lambda$p, $\lambda$q) belongs within the MIR range.

Sensing elements associated with transmittance spectra 1510 may be 'color' ICE devices designed from principal components analysis on a VIS spectrum database. In some embodiments, sensing elements designed to have VIS spectra 1510 may be desirable for reconstructing high-resolution VIS spectra. In some embodiments, sensing elements with NIR transmittance spectra 1511 (e.g., in the band from 1615 to 2280 nm), and MIR transmittance spectrum 1512 (e.g., in the band from 2500 nm to 3300 nm) may provide desirable inputs to a MIMO or a MISO transformation to reconstruct a high-resolution VIS spectrum (e.g., MIMO transformation 1100 and MIMO transformation 1200). Thus, in some embodiments, when measuring light oil and medium oil, a nonlinear transformation as disclosed herein enables prediction of high-resolution VIS spectra without using sensing elements configured to respond in the VIS spectral range.

Figure 16:
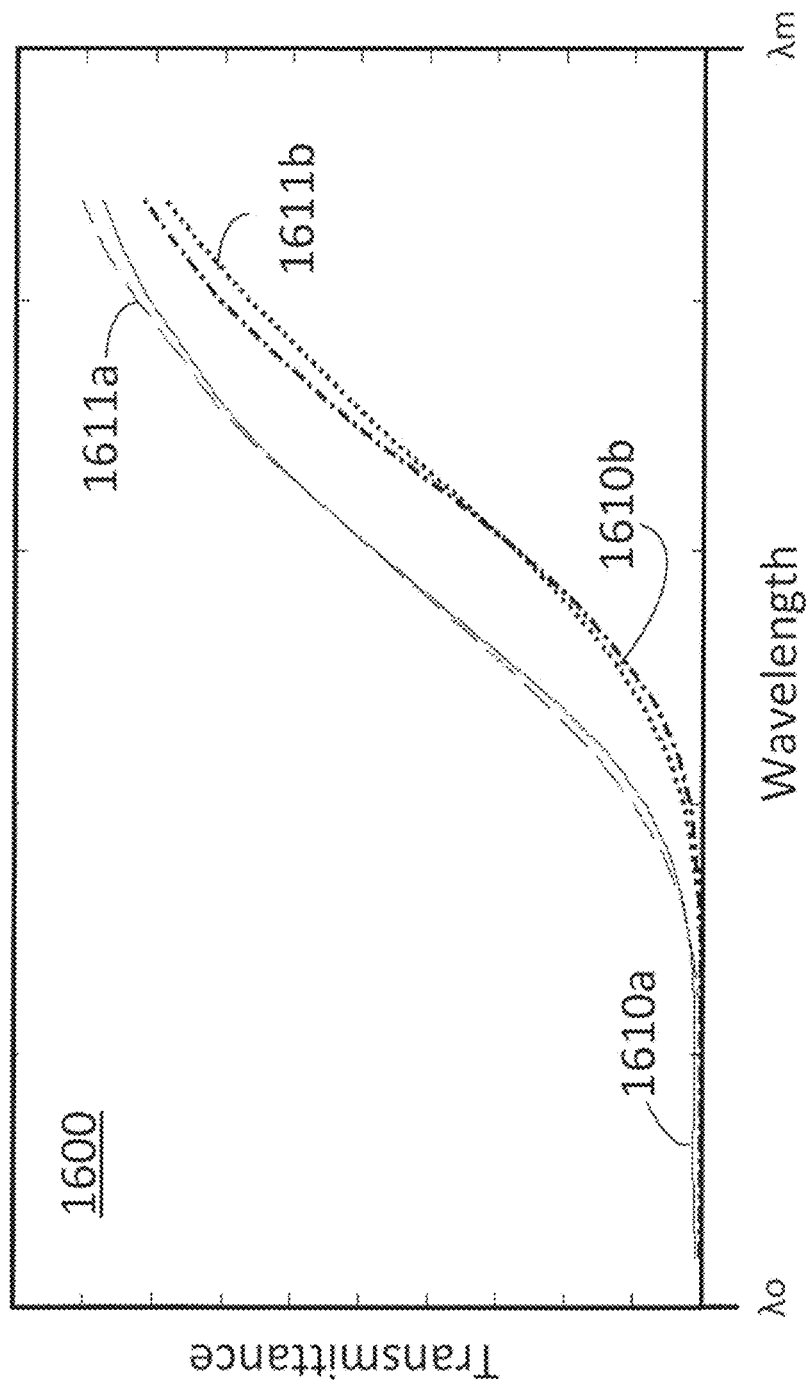
FIG. 16 is a plot illustrating transmittance spectra in a first spectral region reconstructed with a sensing element configured for a second spectral region compared to spectra in the first spectral region reconstructed with a sensing element configured for the first and second spectral regions.

FIG. 16 is a plot 1600 illustrating transmittance spectra 1610$a$ and 1610$b$ for two samples 'a' and 'b' in a first spectral region reconstructed with a sensing element configured for a second spectral region (hereinafter collectively referred to as spectra 1610). Plot 1600 includes transmittance spectra 1611$a$ and 1611$b$ for the two samples 'a' and 'b' in the first spectral region, and reconstructed with a sensing element configured for the first spectral region (hereinafter collectively referred to as spectra 1611). In some embodiments, the first spectral region may be the VIS region, and the second spectral region may be any one of the UV region, the NIR region, or the MIR region. More generally, any other combination of the UV, VIS, NIR or MIR ranges as the first or second spectral regions may be possible.

Without limitation, the nonlinear model used to recover spectra 1610 and 1611 is a MIMO transformation (e.g., MIMO transformation 1100, cf. FIG. 11). Accordingly, wavelength range ($\lambda_o$, $\lambda_m$) in plot 1600 may include the wavelength range from 450 to 1000 nanometers. The agreement between spectra 1610 and 1611 suggests that an optical computing device may reconstruct high-resolution VIS spectra using NIR and MIR sensing elements alone, according to some embodiments. Without limitation, embodiments consistent with the present disclosure may be extended to re-construct high-resolution visible spectra in wavelength ranges other than the VIS by using available spectra in a calibration library, through an enhanced machine learning.

Figure 17:
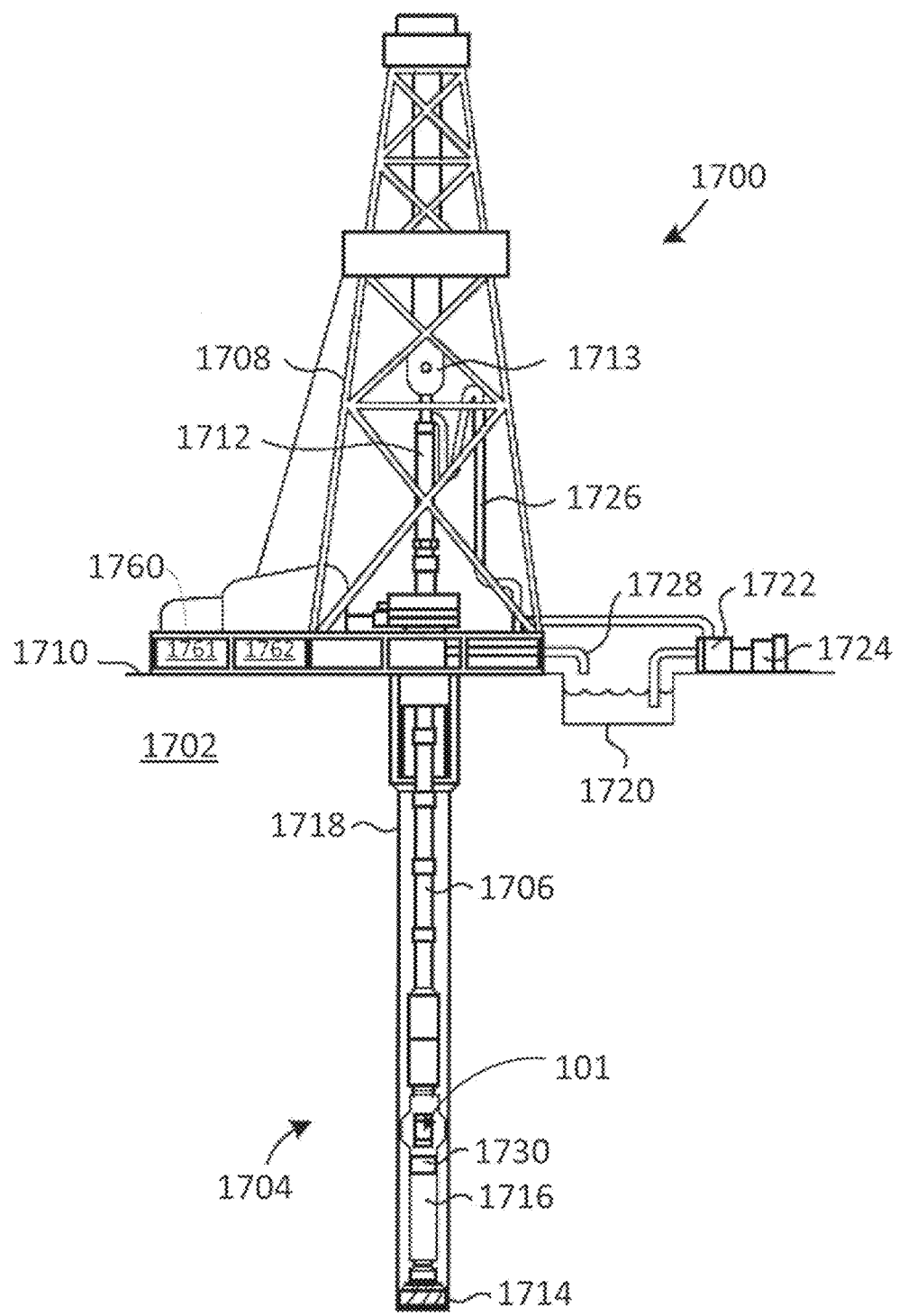
FIG. 17 illustrates a logging while drilling system including a sensor that uses an optical computing device improved with an add-on ICE.

FIG. 17 illustrates a logging-while-drilling system 1700 including an optical computing device (e.g., optical computing devices 101, cf. FIGS. 1A-B) for obtaining measurements of a formation fluid. Optical computing device 101 is installed on a downhole tool 1730 and used to modify a drilling parameter, such as a penetration rate or a drilling direction, in a measurement-while-drilling (MWD) or a logging-while-drilling (LWD) operation, according to estimated wellbore or formation fluid properties. Boreholes may be created by drilling into the earth 1702 using drilling system 1700. Drilling system 1700 may be configured to drive a bottom hole assembly (BHA) 1704 positioned or otherwise arranged at the bottom of a drill string 1706 extended into the earth 1702 from a derrick 1708 arranged at the surface 1710. Derrick 1708 includes a kelly 1712 and a traveling block 1713 used to lower and raise the kelly 1712 and the drill string 1706.

The BHA 1704 may include a drill bit 1714 operatively coupled to a tool string 1716 which may be moved axially within a drilled wellbore 1718 as attached to the drill string 1706. During operation, drill bit 1714 penetrates the earth 1702 and thereby creates the wellbore 1718. The BHA 1704 provides directional control of the drill bit 1714 as it advances into earth 1702. Tool string 1716 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, measurement tools may be self-contained within the tool string 1716, as shown.

Fluid or "mud" from a mud tank 1720 may be pumped downhole using a mud pump 1722 powered by an adjacent power source, such as a prime mover or motor 1724. The mud may be pumped from the mud tank 1720, through a stand pipe 1726, which feeds the mud into the drill string 1706 and conveys the same to drill bit 1714. The mud exits one or more nozzles arranged in drill bit 1714 and in the process cools drill bit 1714. After exiting drill bit 1714, the mud circulates back to surface 1710 via the annulus defined between wellbore 1718 and drill string 1706, and in the process, returns drill cuttings and debris to the surface. The cuttings and mud mixture are passed through a flow line 1728 and are processed such that a cleaned mud is returned down hole through the stand pipe 1726 once again.

BHA 1704 may further include downhole tool 1730 having the optical computing device 101, as described herein with reference to FIGS. 1A and 1B. Optical computing device 101 in downhole tool 1730 may be controlled from the surface 1710 by a controller 1760 having a processor 1761 and a memory 1762. Accordingly, memory 1762 may store commands that, when executed by processor 1761, cause controller 1760 to perform at least some steps in methods consistent with the present disclosure. Controller 1760 may be communicatively coupled with optical computing device 101 via a transmission line through borehole 1718. Thus, data collected with optical computing device 101 may be transferred to controller 1760, and commands and instructions adjusting drilling parameters from controller 1760 may be conveyed to drill bit 1714.

Figure 18:
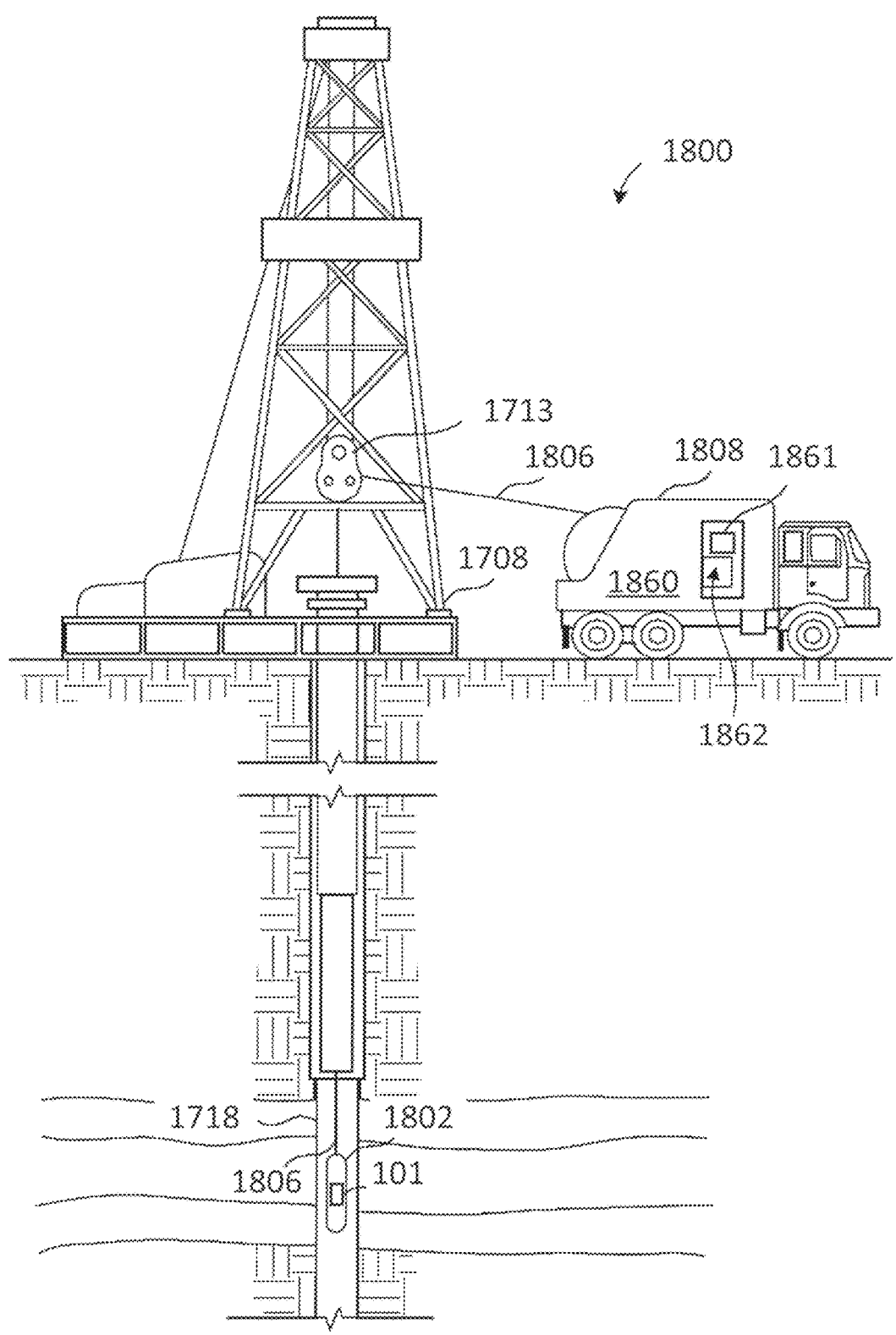
FIG. 18 illustrates a wireline system configured to obtain high-resolution spectral data of a sample during formation testing and sampling with an optical computing device.

FIG. 18 illustrates a wireline system 1800 configured to measure a formation fluid with the optical computing device 101 during formation testing and sampling. Wireline system 1800 may be configured to use a formation tester and calibrated optical computing device 101 to determine types of formation fluids and the associated characteristics through sampling after drilling of wellbore 1718 is complete. System 1800 may include a downhole tool 1802 that forms part of a wireline logging operation that can include the optical computing device 101 as described herein, as part of a downhole measurement tool. System 1800 may include derrick 1708 that supports traveling block 1713. Wireline logging tool 1802, such as a probe or sonde, may be lowered by wireline or logging cable 1806 into borehole 1718. Tool 1802 may be lowered to a potential production zone or a region of interest in the wellbore, and used in conjunction with other components of the formation tester such as packers and pumps to perform well testing and sampling. Optical computing device 101 may be configured to measure optical responses of the formation fluids, and any measurement data generated by downhole tool 1802 and its associated optical computing device 101 can be processed in real-time for decision-making, or communicated to a surface logging facility 1808 for storage, processing, and/or analysis. Logging facility 1808 may be provided with electronic equipment 1810, including processors for various types of signal processing. Electronic equipment 1810 may include a controller 1860 having a processor 1861 and a memory 1862. Accordingly, memory 1862 may store commands that, when executed by processor 1861, cause controller 1860 to perform at least some steps in methods consistent with the present disclosure. Controller 1860 may be communicatively coupled with optical computing device 101 via a transmission line through borehole 1718. Thus, data collected with optical computing device 101 may be transferred to controller 1860, and commands and instructions from controller 1860 may be conveyed to downhole tool 1802.

Figure 19:
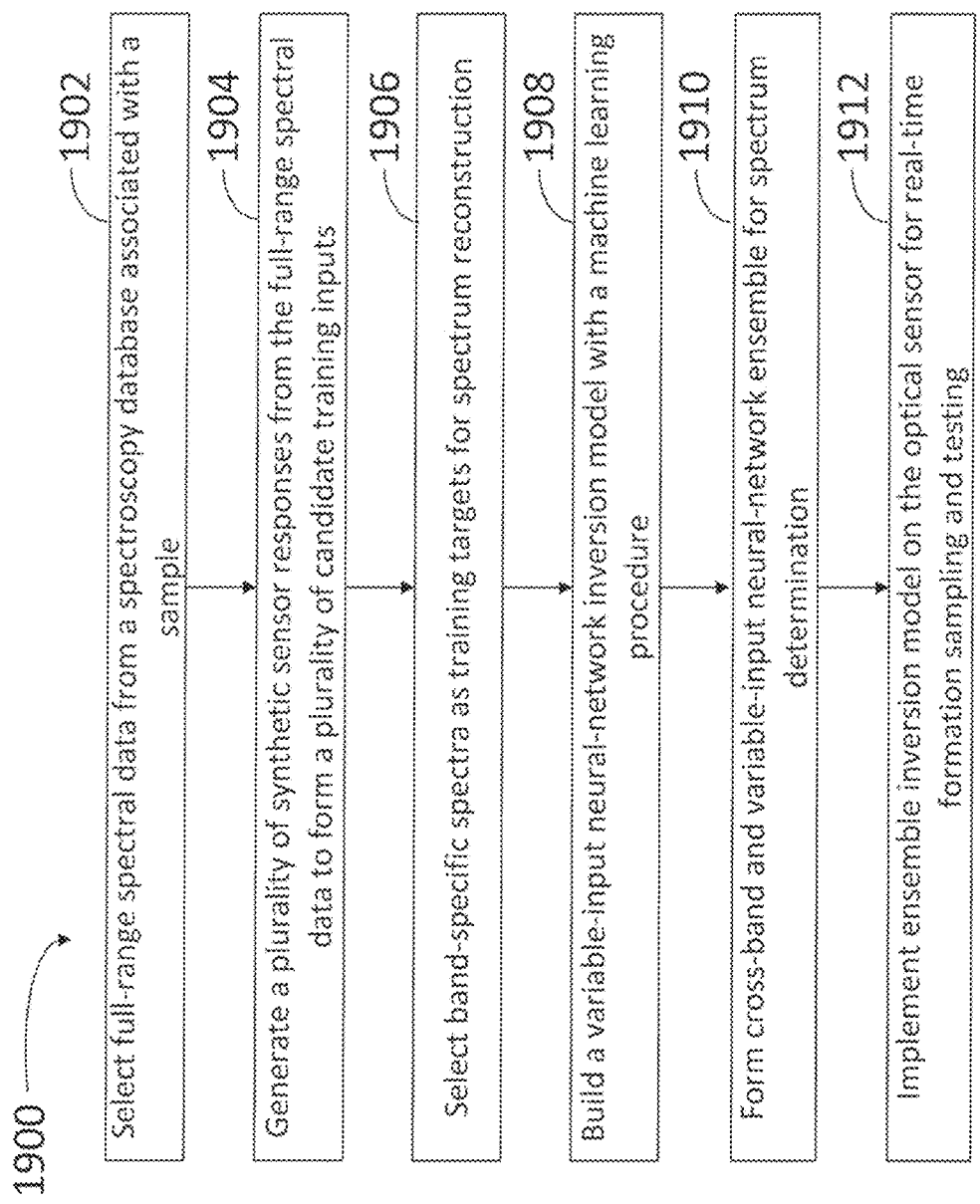
FIG. 19 illustrates a flow chart including steps in a method for obtaining a nonlinear model to recover high-resolution spectral data of a formation fluid from optical computing device measurements.

FIG. 19 illustrates a flow chart including steps in a method 1900 for obtaining a nonlinear model to recover high-resolution spectral data of a formation fluid from optical computing device measurements. The nonlinear model in method 1900 may use as inputs a plurality of sensing signals from a plurality of sensing elements in the optical computing device (e.g., sensing signals 135, sensing elements 100 and optical computing device 101, cf. FIGS. 1A-B). The nonlinear model in method 1900 may include a MIMO transformation, or a MISO transformation using neural networks with machine learning algorithms (e.g., MIMO transformation 1100 and MISO transformation 1200, cf. FIGS. 11 and 12). The machine learning algorithm may be implemented by accessing a library of calibration spectral data collected under controlled conditions by a high-resolution spectrometer. The nonlinear model obtained through method 1900 may be stored as instructions or commands in a memory and configured for execution by a processor, the memory and the processor being part of a controller communicatively coupled to the optical computing device (e.g., controllers 160, 1760 and 1860, processors 161, 1761, and 1861, and memories 162, 1762, and 1862, cf. FIGS. 1A, B, FIG. 17 and FIG. 18). The controller may perform at least some of the steps in method 1900 when the processor executes commands stored in the memory.

Methods consistent with the present disclosure may include at least some, but not all of the steps illustrated in method 1900, performed in a different sequence. Furthermore, methods consistent with the present disclosure may include at least two or more steps as in method 1900 performed overlapping in time, or almost simultaneously.

Step 1902 includes selecting a full range spectral data from a spectroscopy database associated with a sample. In some embodiments, step 1902 includes selecting full-range spectral data from a standard PVT spectroscopy database associated with a sample (e.g., a hydrocarbon fluid). The spectroscopy database may include measurement data from typical heavy oil, medium oil, light oil, gas condensates, gas, water and other non-petroleum fluids spanned over visible, NIR and MIR wavelength range.

Step 1904 includes generating a plurality of synthetic optical computing device responses on the spectral data of step 1902 to form a plurality of candidate training inputs. Step 1904 may include calculating the synthetic optical computing device response on each channel or each optical computing device element. Accordingly, step 1904 may include forming a dot product of a fluid transmittance spectroscopy data with the transmittance spectrum of a particular sensing element responding to a light source. The collection of such optical computing device responses over a variety of wavelength ranges constitutes multi-band optical inputs used as candidate training inputs for inverse modeling in determining fluid spectrum.

In some embodiments, step 1904 may include converting sensing signals from an optical computing device into synthetic sensor responses using an optical data transformation algorithm, or an optical data standardization algorithm. Accordingly, the optical data transformation algorithm or the optical data standardization algorithm may include a nonlinear model obtained through a machine learning protocol.

Step 1906 includes selecting band-specific spectra as training targets for spectrum reconstruction. The selected spectral data in step 1906 could be a subset of full-range spectroscopy data in step 1902, such as VIS spectra, UV spectra, NIR spectra and MIR spectra, depending on the focus or the interest of inversion algorithm.

Step 1908 includes building a variable input neural-network inversion model with a machine learning procedure. Step 1908 performs regularized nonlinear machine learning with neural networks, including at least one of a MIMO transformation or a MISO transformation. The inversion algorithm is input dependent, and can be calibrated in conjunction with use of backward or forward stepwise input selection routines. The candidate algorithms calibrated with different inputs construct a model base for spectrum reconstruction. In some embodiments, step 1908 may include adjusting a plurality of coefficients for a hyperbolic tangent sigmoid transfer function in a multiple layer neural network model, as disclosed herein (e.g., coefficients 1115, 1116, 1125, 1126, 1215, 1216, 1225, 1226, 1235 and 1236, cf. FIGS. 11 and 12, and Eqs. 10-12). Further, adjusting the plurality of coefficients may include comparing an output value from the nonlinear model with a calibration or target value obtained from the spectral database to minimize the difference. For example, step 1908 may include computing the output value as a plurality of averages over a plurality of wavelength ranges, and computing the calibration or target value as the plurality of averages over the same wavelength ranges using spectra in the spectral database.

Step 1910 includes forming a cross-band and variable input neural-network ensemble for spectrum determination. Step 1910 may include forming a plurality of nonlinear models, each nonlinear model having a set of coefficients selected according to step 1908. Step 1910 further includes building a cross-band and variable-input neural network ensemble with more-than-one member neural network based on the overall performance of training, validation and testing data for robust estimation of fluid spectrum.

Step 1912 includes implementing an ensemble inversion algorithm on the optical computing device for real-time formation sampling and testing. In some embodiments, step 1912 implements the ensemble inversion algorithm into real-time data processing software and applies the algorithm during formation sampling and testing, typically with use of a wireline formation tester (e.g., downhole tool 1802, cf. FIG. 18). In some embodiments, step 1912 may further include using the recovered high-resolution spectrum with additional sensor inputs for estimating fluid composition and other properties. Additional sensor inputs may include a fluid pressure, a fluid temperature or a fluid density. Accordingly, the additional fluid computational models may share the data pre-processing and the synthetic sensor data transformation in the optical computing device with the nonlinear model of method 1900.

Figure 20:
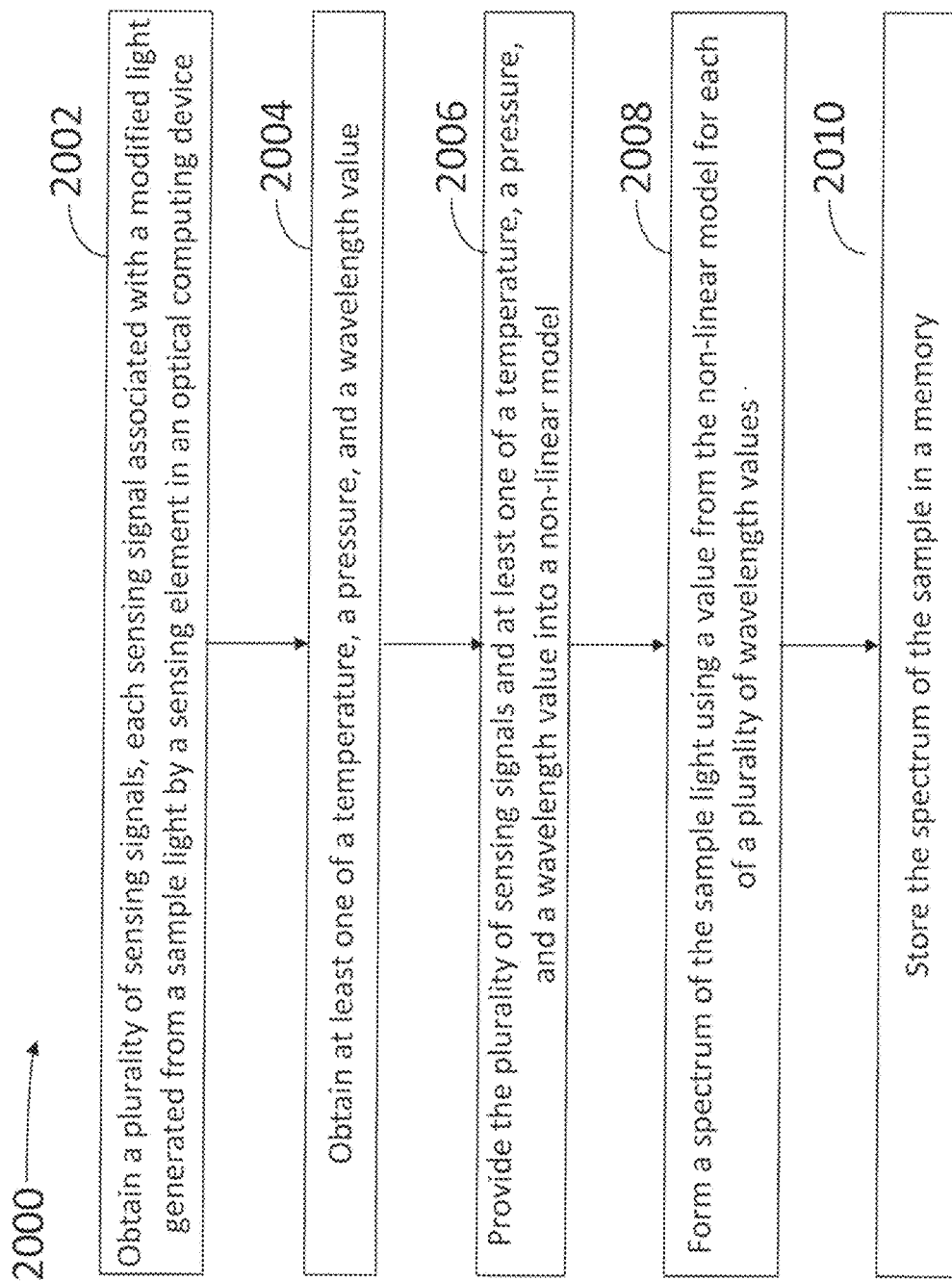
FIG. 20 illustrates a flow chart including steps in a method for obtaining high-resolution spectral data of a formation fluid from optical computing device measurements.

FIG. 20 illustrates a flow chart including steps in a method 2000 for obtaining high-resolution spectral data of a formation fluid from optical computing device measurements. Method 2000 may be performed at least partially by an optical computing device including a plurality of sensing elements for each sensor to be calibrated with a plurality of reference fluids (e.g., optical computing device 101 and sensing elements 100, cf. FIGS. 1A, B) for recovering a high-resolution spectrum of a sample. The sample may generate a sample light received by the optical computing device for processing according to methods consistent with the present disclosure. In addition, method 2000 may also be implemented at least partially with a controller having a processor and a memory (e.g., controllers 160, 1760, and 1860 processors 161, 1761, and 1861 and memories 162, 1762, and 1862, cf. FIGS. 1A-B, 17 and 18). The controller may perform at least some of the steps in method 2000 when the processor executes commands stored in the memory.

Methods consistent with the present disclosure may include at least some, but not all of the steps illustrated in method 2000, performed in a different sequence. Furthermore, methods consistent with the present disclosure may include at least two or more steps as in method 2000 performed overlapping in time, or almost simultaneously.

Step 2002 includes obtaining a plurality of sensing signals, each sensing signal associated with a modified light generated from a sample light by a sensing element in an optical computing device.

Step 2004 includes obtaining at least one of a temperature, a pressure, and a wavelength value. Step 2004 may also include obtaining a density value, associated with a density of a fluid generating the sample light.

Step 2006 includes providing the plurality of sensing signals and at least one of a temperature, a pressure, and a wavelength value into a nonlinear model. The nonlinear model in step 2006 may be any one of a MIMO transformation or a MISO transformation, as disclosed herein (e.g., MIMO transformation 1100 and MISO transformation 1200, cf. FIGS. 11 and 12). In some embodiments, step 2006 includes transmitting the plurality of sensing signals to the controller (e.g., to a controller at the surface of a wireline or a logging while drilling application).

Step 2008 includes forming a spectrum of the sample light using a value from the nonlinear model for each of a plurality of wavelength values. Step 2010 includes storing the spectrum of the sample in the memory of the controller.

Embodiments disclosed herein include:

A. A system, including an optical computing device that includes an optical multiplexer that receives a sample light generated by an optical interaction between a sample and an illumination light, at least two sensing elements that optically interact with the sample light to generate at least a first modified light and a second modified light, and a detector that measures a property of the first and second modified lights separately to generate a first signal and a second signal, respectively. The system may also include a controller including a processor and a memory, wherein the processor receives the first and the second signals and determines a spectral data value of the sample light with high spectral resolution.

B. A method including obtaining a plurality of sensing signals with an optical computing device, each sensing signal being associated with a modified light generated from a sample light optically interacting with a sensing element in the optical computing device. The method also includes obtaining a plurality of synthetic responses using a sensing matrix and a sparse dictionary having a plurality of preselected basis functions associated with a plurality of sparse coefficients in a sparse vector, adjusting the plurality of sparse coefficients by matching the plurality of sensing signals with the plurality of synthetic responses, and forming a spectrum using the plurality of sparse coefficients and the plurality of basis functions in the sparse dictionary.

C. A method, including selecting full-range spectral data from a spectroscopy database associated with a sample and generating a plurality of synthetic sensor responses from the full-range spectral data to form a corresponding plurality of candidate training inputs. The method may also include selecting band-specific sample spectra as training targets for a spectrum reconstruction, building an input-dependent neural network inversion model with a machine-learning procedure, forming a cross-band and variable input neural-network ensemble for spectrum determination, and implementing an ensemble inversion model on the optical computing device for real-time formation sampling and testing.

D. A method, including obtaining a plurality of sensing signals with an optical computing device, each sensing signal being associated with a modified light generated from a sample light optically interacting with a sensing element in the optical computing device. The method may also include obtaining a parameter value of at least one of a temperature, a pressure, and a wavelength, providing the plurality of sensing signals and the parameter value into a nonlinear model, and forming a spectrum of the sample light using a spectral value derived from the nonlinear model for each of a plurality of parameter values.

Each of embodiments A, B, C, and D may have one or more of the following additional elements in any combination. Element 1, further including a light source that generates the illumination light, wherein the controller transmits commands to the light source to control and modify the illumination light. Element 2, wherein the optical multiplexer separates the first and second modified lights in time. Element 3, wherein the optical multiplexer separates the first and second modified lights in space. Element 4, wherein the first and second modified lights are associated with first and second spectral bands, respectively, and the first and second spectral bands are selected from the group consisting of the ultra-violet region, the visible region, the near-infrared region, and the mid-infrared region. Element 5, wherein the memory stores instructions which, when executed by the processor, cause the controller to perform a linear regression to determine the spectral data value. Element 6, wherein the memory stores instructions which, when executed by the processor, cause the controller to execute a nonlinear model to determine the spectral data value. Element 7, wherein the optical computing device is included in a wireline system extended into a wellbore for formation testing and sampling, and wherein the sample is a formation fluid, the controller is a surface device, and the memory stores a plurality of spectral data values. Element 8, wherein the optical computing device is included in a downhole drilling tool and used to modify a drilling parameter during drilling operations, and wherein the sample is a formation fluid, the controller is a surface device, and the memory stores a plurality of spectral data values. Element 9, wherein the controller is included in the downhole formation tester or drilling tool.

Element 10, further including adjusting the plurality of sparse coefficients subject to a condition that the sparse vector has a bounded amplitude. Element 11, further including generating the sample light by interacting an illumination light from a light source with a formation fluid in a wellbore during a wellbore drilling operation or a wireline formation sampling and testing operation. Element 12, further including transmitting the plurality of sparse coefficients to a wellbore surface location, wherein forming the spectrum of the sample light is performed by a controller located at the wellbore surface location. Element 13, further including modifying a drilling parameter according to instructions received from the controller in response to the spectrum of the sample light.

Element 14, wherein forming the cross-band and variable input neural-network ensemble includes using information from a first spectral band as an input and information from a second spectral band as an output, wherein the first spectral band is different from the second spectral band. Element 15, further including building a wavelength-specific, multi-input single-output neural network inversion model, wherein a wavelength is used as an additional input.

Element 16, further including generating the sample light by interacting an illumination light from a light source with a formation fluid in a wellbore during a wellbore drilling operation or a wireline formation sampling and testing operation. Element 17, wherein providing the plurality of sensing signals into a nonlinear model includes transmitting the plurality of sensing signals to a wellbore surface location, wherein forming the spectrum of the sample light is performed by a controller located at the wellbore surface location.

Those skilled in the art will readily appreciate that the methods described herein or large portions thereof, may be automated at some point such that a computerized system may be programmed to transmit data from an optical computing device using an ICE element. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
an optical computing device that includes:
  an optical multiplexer that receives a sample light generated by an optical interaction between a sample and an illumination light;
  at least two sensing elements that optically interact with the sample light to generate at least a first modified light and a second modified light, wherein the at least two sensing elements include respective broadband filters with a spectral profile defined by one or more basis functions associated with calibration spectral data collected from known samples with known properties at a first spectral resolution; and a detector that measures an intensity of the first and second modified lights separately to generate at least a first signal and a second signal, respectively, wherein the at least the first signal and second signal represent a spectrum of the sample light with a second spectral resolution less than the first resolution; and a controller comprising a processor and a memory, wherein the processor receives the at least first and second signals and determines a spectrum of the sample light with the first spectral resolution based on the at least first and second signals and the one or more basis functions associated with the calibration spectral data collected from known samples with known properties at the first spectral resolution.

2. The system of claim 1, further comprising a light source that generates the illumination light, wherein the controller transmits commands to the light source to control and modify the illumination light.

3. The system of claim 1, wherein the optical multiplexer separates the first and second modified lights in time.

4. The system of claim 1, wherein the optical multiplexer separates the first and second modified lights in space.

5. The system of claim 1, wherein the first and second modified lights are associated with first and second spectral bands, respectively, and the first and second spectral bands are selected from the group consisting of an ultra-violet region, a visible region, a near-infrared region, and a mid-infrared region.

6. The system of claim 1, wherein the memory stores instructions which, when executed by the processor, cause the controller to perform a linear regression based on the one or more basis functions to determine the spectrum of the sample light with the first spectral resolution.

7. The system of claim 1, wherein the memory stores instructions which, when executed by the processor, cause the controller to execute a nonlinear model based on the one or more basis functions, cross-band and wavelength inputs to determine the spectrum of the sample light with the first spectral resolution.

8. The system of claim 1, wherein the optical computing device is included in a wireline system extended into a wellbore for formation testing and sampling, and wherein the sample is a formation fluid, the controller is a surface device, and the memory stores a plurality of spectral data values.

9. The system of claim 1, wherein the optical computing device is included in a downhole drilling tool and used to modify a drilling parameter during drilling operations, and wherein the sample is a formation fluid, the controller is a surface device, and the memory stores a plurality of spectral data values.

10. The system of claim 1, wherein the controller is included in a downhole formation tester or a drilling tool.

\* \* \* \* \*